United States Patent [19]

Imai et al.

[11] Patent Number: 6,140,321

[45] Date of Patent: Oct. 31, 2000

[54] POLYMORPHS OF DONEPEZIL HYDROCHLORIDE AND PROCESS FOR PRODUCTION

[75] Inventors: Akio Imai; Hideaki Watanabe; Takashi Kajima; Yasushi Ishihama; Akiyo Ohtsuka; Tomohide Tanaka, all of Ibaraki, Japan

[73] Assignee: Eisai Co., Ltd., Tokyo, Japan

[21] Appl. No.: 08/774,802

[22] Filed: Dec. 30, 1996

[30] Foreign Application Priority Data

Jun. 7, 1996 [JP] Japan .................................. 8-146293

[51] Int. Cl.[7] .......................... A01N 43/46; A01N 43/36; C07D 211/20; C07D 223/00

[52] U.S. Cl. .......................... 514/212; 514/319; 514/321; 514/357; 514/408; 514/422; 514/426; 540/484; 540/596; 540/611; 540/612; 546/197; 546/206; 546/237; 548/400; 548/526; 548/529

[58] Field of Search .................... 546/737, 197, 546/206; 514/212, 319, 321, 357, 408, 422, 429; 540/484, 596, 611, 612; 548/400, 526, 529

[56] References Cited

U.S. PATENT DOCUMENTS 4,895,841  1/1990  Sugimoto et al. ...................... 514/212

FOREIGN PATENT DOCUMENTS 0296560  12/1988  European Pat. Off. .

OTHER PUBLICATIONS

Iimura et al, Chemical Abstract vol. 117 No. 191509, "Prep. of Optically Active Indanone Der. as Acetylcholinesterase Inhibitors" (1992).

*Primary Examiner*—John Kight
*Assistant Examiner*—Raymond Covington
*Attorney, Agent, or Firm*—Birch, Stewart, Kolasch & Birch, LLP

[57] ABSTRACT

Donepezil hydrochloride, 1-benzyl-4-[(5,6-dimethoxy-1-indanon)-2-yl]methylpiperidine hydrochloride, is provided here in the form of four polymorphs which are stable against heat and humidity in the pharmaceutical use. They can be industrially produced. They are specified by peaks in X-ray powder diffraction pattern and absorption peaks in infrared absorption spectra in potassium bromide.

12 Claims, 18 Drawing Sheets

POLYMORPHS OF DONEPEZIL HYDROCHLORIDE AND PROCESS FOR PRODUCTION

FIELD OF THE INVENTION

The present invention relates to the stable polymorphs of Donepezil hydrochloride, that is, 1-benzyl-4-[(5,6-dimethoxy-1-indanon)-2-yl]methyl-piperidine hydrochloride, disclosed in the example 4 of U.S. Pat. No. 4,895,841 or EP-A 296560, having an excellent efficacy as pharmaceuticals, and industrial processes for producing them.

BACKGROUND OF THE INVENTION

Donepezil hydrochloride shows the acetylcholine esterase-inhibitory action and is useful for the treatment of all kinds of senile dementia, in particular being useful for prevention, treatment and amelirolation of Alzheimer Disease. Donepezil hydrochloride is administered orally as usual and it may be placed for distribution and storage in a period of time before the administration. It may then be stored at patient's home for about one month at the maximum because of the property of the target disease. The stability of this medicinal substance (bulk pharmaceutical chemicals) against heat and humidity during the storage period is very important. A more stable medicinal substance of Donepezil hydrochloride is, therefore, desired. It is not known, however, that polymorphs of Donepezil hydrochloride exist. No sufficiently stable medicinal substance of Donepezil hydrochloride has been found.

PRIOR ART

U.S. Pat. No. 4,895,841 discloses in Example 4 that recrystalization of the crude product mixture of Donepezil hydrochloride from ethanol/isopropyl ether afforded a purified Donepezil hydrochloride. If there is a more stable crystalline form of Donepezil hydrochloride for a long period, it is more practical for distribution and storage.

SUMMARY OF THE INVENTION

Regarding the foregoing problems, the present inventors have proceeded with extensive research. As a result, it has been found that novel polymorphs of Donepezil hydrochloride (I) to (IV) can be produced and have an excellent stability, establishing the present invention. The present invention offers the four forms or species of novel polymorphs of Donepezil hydrochloride and industrially excellent processes for producing them.

In detail, the present invention relates to the four polymorphs (I) to (IV) of Donepezil hydrochloride represented by the following chemical structure, the polymorphs being specified by the peaks appearing in the powder X-ray diffraction pattern and infrared absorption spectra in potassium bromide.

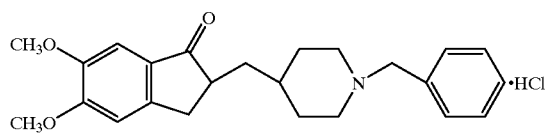

Method and Condition of the Measurement of X-ray Diffraction patterns)

(1) Method of the Measurement

X-ray diffraction patterns were measured on each 100 mg of the samples by the following condition.

(2) Condition of the Measurement

| Target | Cu |
|---|---|
| Filter | monochro |
| Voltage | 40 Kv |
| Current | 20 mA |
| Slit DS | 1, RS 0.15, SS 1 |
| Scan speed | 2 deg/min. |
| Range | 5–30 |

Method and Condition of the Measurement of Infrared Absorption

Infrared absorption spectra in potassium bromide were measured according to the general method recorded in the Japanese Pharmacopoeia.

(1) Polymorphs (I)

Peaks in the powder X-ray diffraction pattern are:

| Diffraction angles (2Θ, °) | Intensity (I/I$_o$) |
|---|---|
| 9.94 | 24 |
| 10.60 | 19 |
| 12.66 | 69 |
| 13.12 | 55 |
| 13.66 | 44 |
| 13.86 | 40 |
| 14.92 | 49 |
| 15.26 | 17 |
| 16.08 | 35 |
| 16.86 | 34 |
| 17.50 | 34 |
| 17.58 | 42 |
| 18.42 | 20 |
| 19.28 | 27 |
| 19.80 | 45 |
| 19.94 | 45 |
| 21.22 | 100 |
| 22.00 | 32 |
| 22.54 | 31 |
| 22.98 | 49 |
| 23.60 | 56 |
| 23.78 | 75 |
| 23.92 | 78 |
| 26.46 | 33 |
| 28.02 | 25 |
| 29.50 | 37. |

Wave numbers (cm$^{-1}$) of infrared absorption spectra in potassium bromide are:
463, 502, 563, 589, 604, 701, 750, 759, 799, 860, 922, 947, 972, 1012, 1038, 1104, 1120, 1128, 1175, 1192, 1218, 1250, 1267, 1316, 1368, 1410, 1433, 1440, 1455, 1472, 1502, 1591, 1606, 1644, 1684, 2412, 2530, 2559, 2595, 2620, 2717, 2840, 2858, 2924, 3004, 3074, 3259, 3373, 3547, 3589 cm$^{-1}$.

(2) Polymorphs (II)

Peaks in the powder X-ray diffraction pattern are:

| Diffraction angles (2Θ, °) | Intensity (I/I$_o$) |
|---|---|
| 7.40 | 8 |
| 9.88 | 100 |

-continued

| Diffraction angles (2Θ, °) | Intensity (I/I$_o$) |
| --- | --- |
| 12.36 | 13 |
| 15.54 | 40 |
| 16.10 | 38 |
| 16.22 | 38 |
| 16.48 | 35 |
| 17.30 | 17 |
| 18.04 | 20 |
| 18.44 | 17 |
| 18.84 | 19 |
| 19.34 | 19 |
| 19.84 | 47 |
| 21.16 | 24 |
| 22.40 | 19 |
| 23.18 | 33 |
| 24.02 | 22 |
| 24.92 | 25 |
| 25.72 | 27 |
| 26.40 | 18 |
| 27.22 | 14. |

Wave numbers (cm$^{-1}$) of infrared absorption spectra in potassium bromide are:

699, 748, 762, 845, 947, 1009, 1035, 1067, 1103, 1118, 1129, 1174, 1193, 1206, 1222, 1247, 1267, 1317, 1365, 1422, 1436, 1456, 1465, 1502, 1592, 1607, 1688, 2412, 2489, 2627, 2846, 2868, 2913, 2928, 3435 cm$^{-1}$.

(3) Polymorphs (III)

Peaks in the powder X-ray diffraction pattern are:

| Diffraction angles (2Θ, °) | Intensity (I/I$_o$) |
| --- | --- |
| 6.56 | 30 |
| 9.94 | 8 |
| 13.00 | 17 |
| 15.00 | 47 |
| 15.26 | 14 |
| 15.74 | 6 |
| 16.48 | 35 |
| 17.42 | 4 |
| 18.10 | 21 |
| 18.50 | 56 |
| 19.50 | 17 |
| 20.10 | 32 |
| 20.94 | 21 |
| 21.66 | 100 |
| 22.32 | 25 |
| 22.92 | 17 |
| 23.92 | 19 |
| 24.68 | 17 |
| 26.00 | 44 |
| 27.20 | 23 |
| 28.02 | 29 |
| 28.22 | 40 |
| 28.60 | 13. |

Wave numbers (cm$^{-1}$) of infrared absorption spectrum in potassium bromide are:

559, 641, 648, 702, 749, 765, 786, 807, 851, 872, 927, 949, 966, 975, 982, 1007, 1034, 1071, 1080, 1111, 1119, 1131, 1177, 1190, 1205, 1217, 1230, 1250, 1265, 1292, 1313, 1367, 1389, 1420, 1438, 1453, 1461, 1470, 1500, 1589, 1605, 1697, 2407, 2419, 2461, 2624, 2641, 2651, 2667, 2837, 2848, 2873, 2924, 2954, 2961, 2993, 3007, 3377, 3433 cm$^{-1}$.

(4) Polymorphs (IV)

Peaks in the powder X-ray diffraction pattern are:

| Diffraction angles (2Θ, °) | Intensity (I/I$_o$) |
| --- | --- |
| 6.24 | 15 |
| 9.66 | 12 |
| 11.04 | 22 |
| 12.12 | 24 |
| 12.54 | 67 |
| 12.76 | 61 |
| 13.98 | 27 |
| 14.42 | 15 |
| 14.88 | 11 |
| 16.34 | 12 |
| 17.46 | 100 |
| 18.12 | 25 |
| 18.60 | 32 |
| 19.06 | 15 |
| 19.98 | 74 |
| 20.42 | 41 |
| 20.62 | 34 |
| 21.30 | 48 |
| 21.80 | 63 |
| 22.58 | 78 |
| 23.04 | 46 |
| 24.00 | 32 |
| 24.54 | 49 |
| 25.14 | 90 |
| 25.36 | 99 |
| 26.06 | 34 |
| 28.10 | 41 |
| 28.58 | 39 |
| 29.30 | 31 |
| 29.44 | 28. |

Wave numbers (cm$^{-1}$) of infrared absorption spectra in potassium bromide are:

401, 431, 459, 467, 490, 506, 518, 561, 586, 606, 631, 651, 709, 758, 766, 857, 944, 1009, 1041, 1106, 1119, 1132, 1213, 1225, 1265, 1304, 1318, 1429, 1458, 1470, 1500, 1589, 1605, 1630, 1647, 1683, 2562, 2577, 2608, 2634, 2689, 2717, 2836, 2924, 2949, 2989, 3007, 3032, 3061, 3322, 3376, 3422 cm$^{-1}$.

Melting points of the novel Polymorphs (I) to (IV) disclosed in the present invention are different from that of example 4 in U.S. Pat. No. 4,895,841.

A melting point in U.S. Pat. No. 4,895,841 is 211–212° C. (decompsition).

Melting point of the polymorph (I): 225–226° C. (decompsition)

Melting point of the polymorph (II): 224–226° C. (decompsition)

Melting point of the polymorph (III): 229–231° C. (decomposition)

Melting point of the polymorph (IV): 226–228° C. (decomposition).

Furthermore, the thermogravimetric and differential thermal analysis (TG-DTA) of the present polymorphs measured under the following condition show different patterns from the prior one. It is noted accordingly that their crystalline forms are completely different from the prior one.

{Method and condition of the thermogravimetric and differential thermal analysis (TG-DTA)}

About 3 to 6 mg of Samples were taken and subjected to thermal analysis under the following condition.

| | |
|---|---|
| Reference | empty |
| Scan speed | 5° C./min. |
| Sampling | 0.7 sec. |
| Upper limit | 300° C. |
| Lower limit | Room temperature. |

Detailed processes for preparing the novel polymorphs are as follows. In these processes, "Donepezil" means a free base of the Donepezil hydrochloride, i.e., 1-benzyl-4-[(5,6-dimethoxy-1-indanon)-2-yl]methylpiperidine.

(1) Processes for preparing the polymorph (I) are:

(1-1) Recrystalization of Donepezil hydrochloride from methanol, (1-2) Dissolving Donepezil hydrochloride in methanol, followed by addition of diethyl ether or diisopropyl ether, (1-3) Dissolving Donepezil in methanol, followed by addition of hydrochloric acid or hydrogen chloride, (1-4) Dissolving Donepezil in ethanol, followed by addition of diisopropyl ether, and hydrochloric acid or hydrogen chloride successively; or (1-5) Dissolving Donepezil in ethanol, followed by addition of hydrochloric acid or hydrogen chloride, and diisopropyl ether successively, then filtration of the crystals immediately after separation.

Process (1-5) is preferred. This process is illustrated in Example 7.

(2) Processes for preparing the polymorph (II) are:

(2-1) Dissolving Donepezil hydrochloride in ethanol, followed by addition of diethyl ether or diisopropyl ether, (2-2) Dissolving Donepezil hydrochloride in ethanol, followed by addition of diisopropyl ether, then filtration of the crystals after 10 to 30 minutes from the separation, (2-3) Dissolving Donepezil and hydrochloric acid or hydrogen chloride in ethanol, followed by addition of diethyl ether, (2-4) Dissolving Donepezil in ethanol, followed by addition of hydrochloric acid or hydrogen chloride, then concentration, (2-5) Dissolving Donepezil in ethanol, followed by addition of hydrochloric acid or hydrogen chloride, and diisopropyl ether successively; or (2-6) Dissolving Donepezil in ethanol, followed by addition of hydrochloric acid or hydrogen chloride, and diisopropyl ether successively, then filtration of the crystals after 10 to 60 minutes, preferably 10 to 30 minutes from the separation.

Process (2-6) is preferred. This process is illustrated in Example 14.

(3) Processes for preparing the polymorph (III) are:

(3-1) Dissolving Donepezil hydrochloride in ethanol, followed by addition of diethyl ether, (3-2) Dissolving Donepezil hydrochloride in dichloromethane, followed by addition of n-hexane, (3-3) Dissolving Donepezil in acetone, followed by addition of hydrochloric acid or hydrogen chloride, (3-4) Dissolving Donepezil in ethyl acetate, followed by addition of hydrochloric acid or hydrogen chloride, (3-5) Dissolving Donepezil in ethanol, followed by addition of hydrochloric acid or hydrogen chloride, then addition of at least one solvent selected from diethyl ether, diisopropyl ether and n-hexane, (3-6) According to a process (3-5) wherein the selected solvent is diisopropyl ether, filtration of the crystals after 1 hour, preferably 2 hours, more preferably 6 hours from the separation; or (3-7) Heating of the polymorph (I) or (II).

Processes (3-5) and (3-6) are preferred. These processes are illustrated, respectively, in Examples 23 and 18.

(4) A process for preparing the polymorph (IV) is:

(4-1) Humidification of the polymorph (II).

Process (4-1) is illustrated in Example 24.

The aforementioned processes (1-5), (2-6) and (3-6) comprise dissolving Donepezil in ethanol, followed by addition of hydrochloric acid or hydrogen chloride, and then adding diisopropyl ether. Anyone of these processes can produce polymorph (I), (II) or (III) by controlling an interval in time taken from recrystallization to isolation of crystals by filtration. These time lag may differ by the crystallization conditions, such as temperature, stirring velocity and a volume of a solvent. The following may be usually used.

(1) Filtration of the crystals immediately after separation affords the polymorph (I).

(2) Filtration of the crystals after 10 to 60 minutes, preferably 10 to 30 minutes from the separation affords the polymorph (II).

(3) Filtration of the crystals after 1 hour, preferably 2 hours, more preferably 6 hours from the separation affords the polymorph (III).

The invention provides a method for treating a disease accompanied by acetylcholinesterase activity by administering to a human patient a pharmacologically effective amount of the Donepezil hydrochloride in the form of polymorph as above for inhibiting the acetylcholinesterase activity.

The invention further provides a therapeutical composition which comprises a pharmacologically effective amount of Donepezil hydrochloride in the form of polymorph as above and a pharmacologically acceptable carrier.

The compound in the form of polymorph of the present invention is effective for treatment, prevention, remission, improvement, etc. of various kinds of senile dementia, particularly senile dementia of the Alzheimer type; cerebrovascular diseases accompanying cerebral apoplexy, e.g. cerebral hemorrhage or cerebral infarcts, cerebral arteriosclerosis, head injury, etc.; and aprosexia, disturbance of speech, hypobulia, emotional changes, recent memory disturbance, hallucinatory-paranoid syndrome, behavioral changes, etc. accompanying encephalitis, cerebral palsy, etc.

Further, the compound in the form of polymorph of the present invention has a strong and highly selective acetylcholinesterase action, which renders the compound of the present invention useful also as a pharmaceutical based on this kind of action.

Specifically, the compound in the form of polymorph of the present invention is effective for, for example, Huntington's chorea, Pick's disease and delayed ataxia or tardive dyskinesia other than senile dementia of the Alzheimer type.

When the compound in the form of polymorph of the present invention is used as a pharmaceutical for these diseases, it may be orally or parenterally administered. In general, it is parenterally administered in the form of injections, such as intravenous, subcutaneous, and intramuscular injections, suppositories, or sublingual tablets. The dose will remarkably vary depending upon the symptom; age, sex, weight, and sensitivity of patients; method of administration; time and intervals of administration and properties, dispensing, and kind of pharmaceutical preparations; kind of effective ingredients, etc., so that there is no particular limitation with respect to the dose. Normally the compound may be administered in a dose of about 1.0 to 300 mg, preferably 1 to 100 mg, per day per adult, ordinarily in one to four portions.

Pharmaceutical preparations in the dosage form of, e.g., injections, suppositories, sublingual tablets, tablets, and capsules are prepared according to a method which is commonly accepted in the art.

In preparing injections, the effective ingredient is blended, if necessary, with a pH modifier, a buffer, a suspending agent, a solubilizing agent, a stabilizer, a tonicity agent, a preservative, etc., followed by preparation of an intravenous, subcutaneous, or intramuscular injection according to an ordinary method. In this case, if necessary, it is possible to lyophilize these preparations according to an ordinary method.

Examples of the suspending agents include methylcellulose, Polysorbate 80, hydroxyethylcellulose, acacia, powdered tragacanth, sodium carboxymethylcellulose, and polyoxyethylene sorbitan monolaurate.

Examples of the solubility agent include polyoxyethylene hydrogenated castor oil, Polysorbate 80, nicotinamide, polyoxyethylene sorbitan monolaurate, Macrogol, and an ethyl ester of castor oil fatty acid.

Examples of the stabilizer include sodium sulfite, sodium metasulfite and ether, and examples of the preservative include methyl p-hydroxybenzoate, ethyl p-hydroxybenzoate, sorbic acid, phenol, cresol, and chlorocresol.

EXAMPLES

Figure 1:
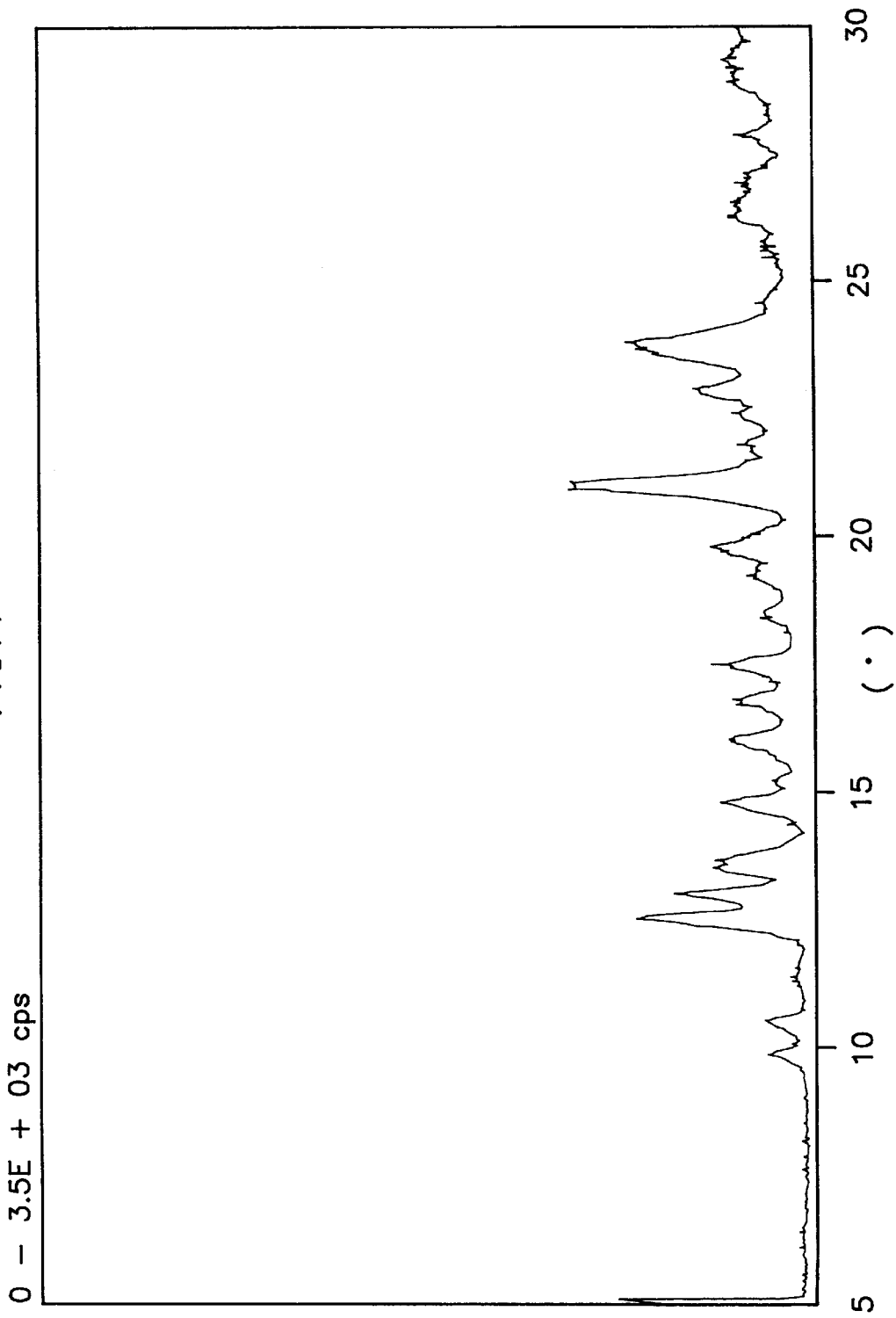
FIG. 1 is powder X-ray diffraction pattern of the polymorph (I).
Figure 2:
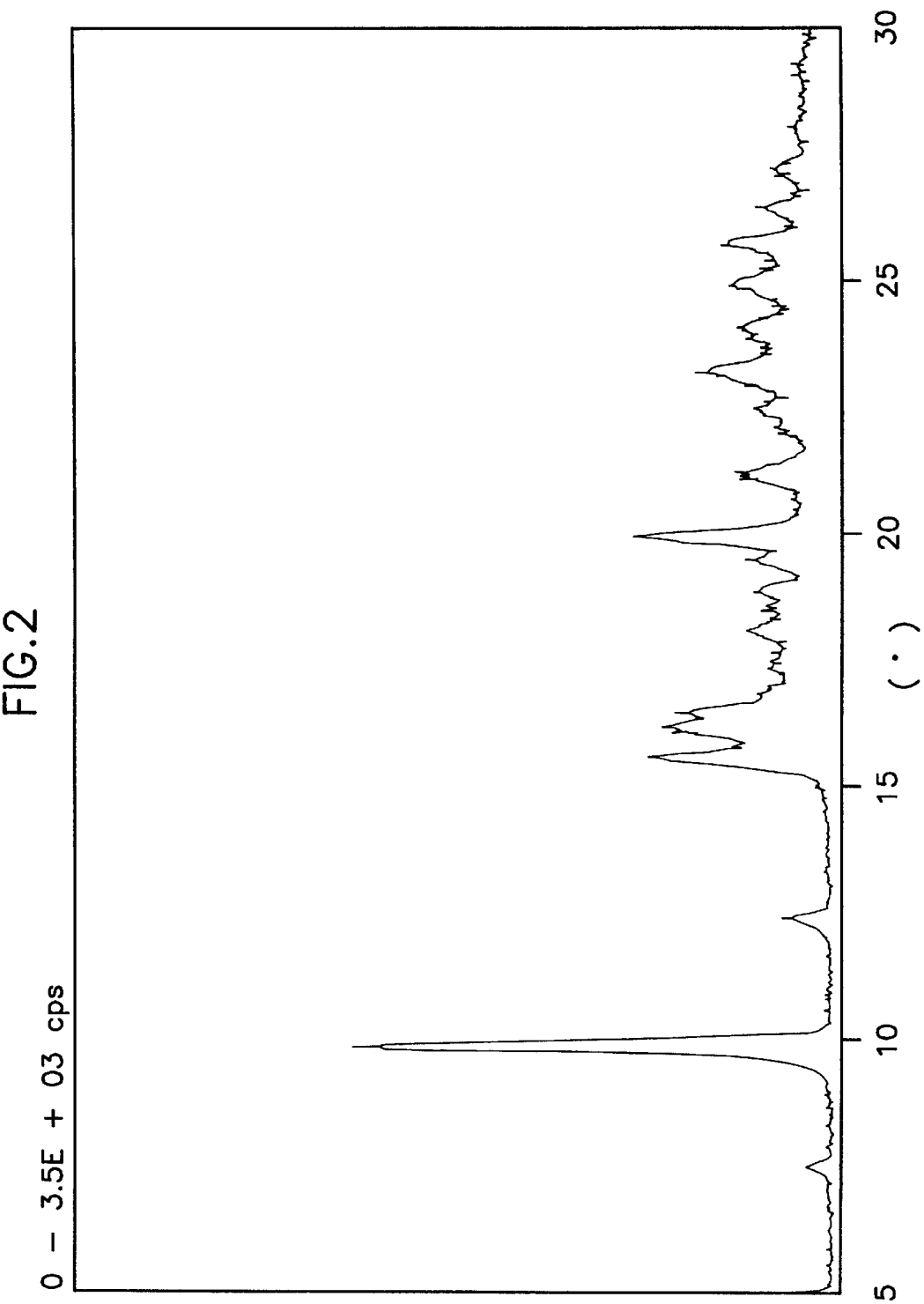
FIG. 2 is powder X-ray diffraction pattern of the polymorph (II).
Figure 3:
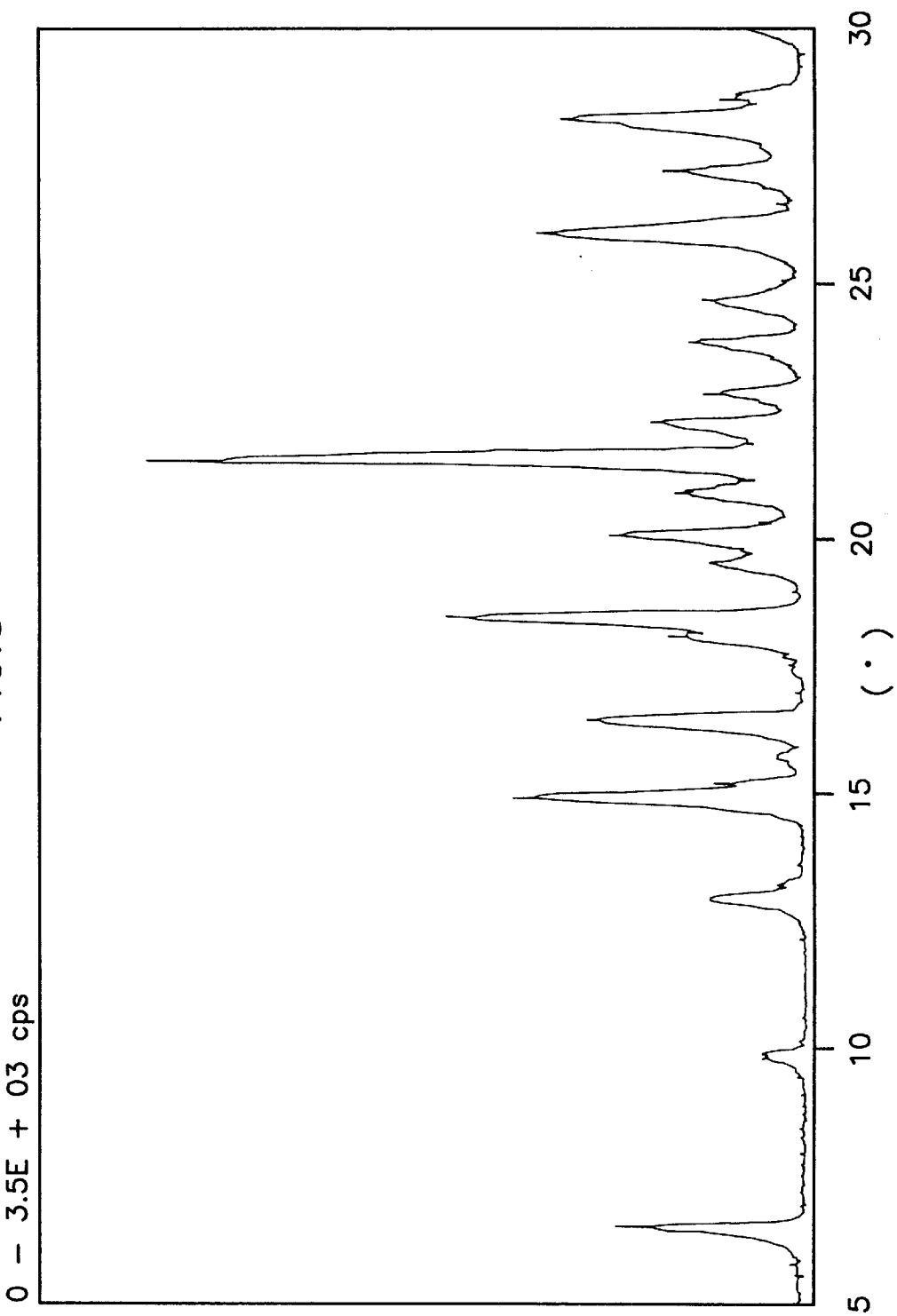
FIG. 3 is powder X-ray diffraction pattern of the polymorph (III).
Figure 4:
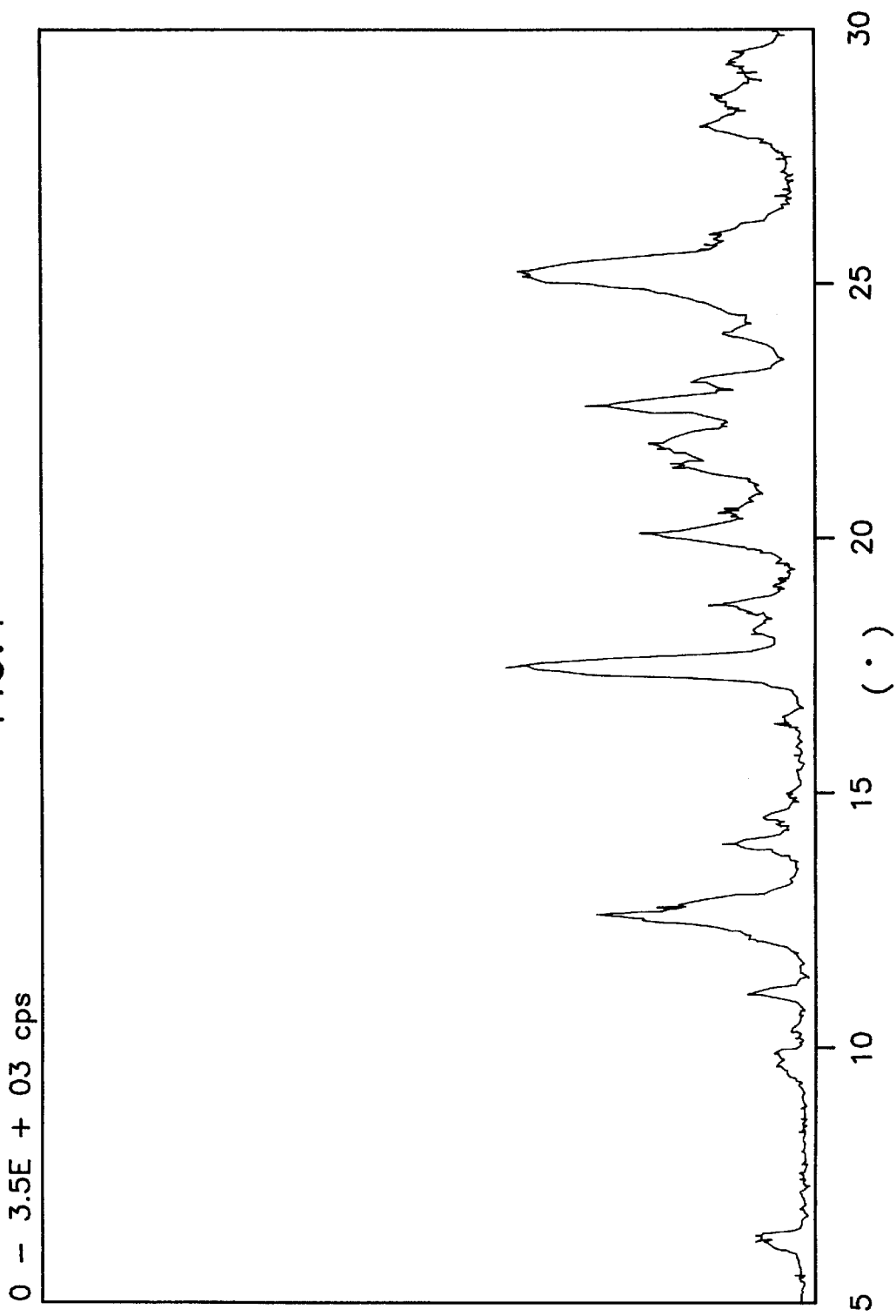
FIG. 4 is powder X-ray diffraction pattern of the polymorph (IV).
Figure 5:
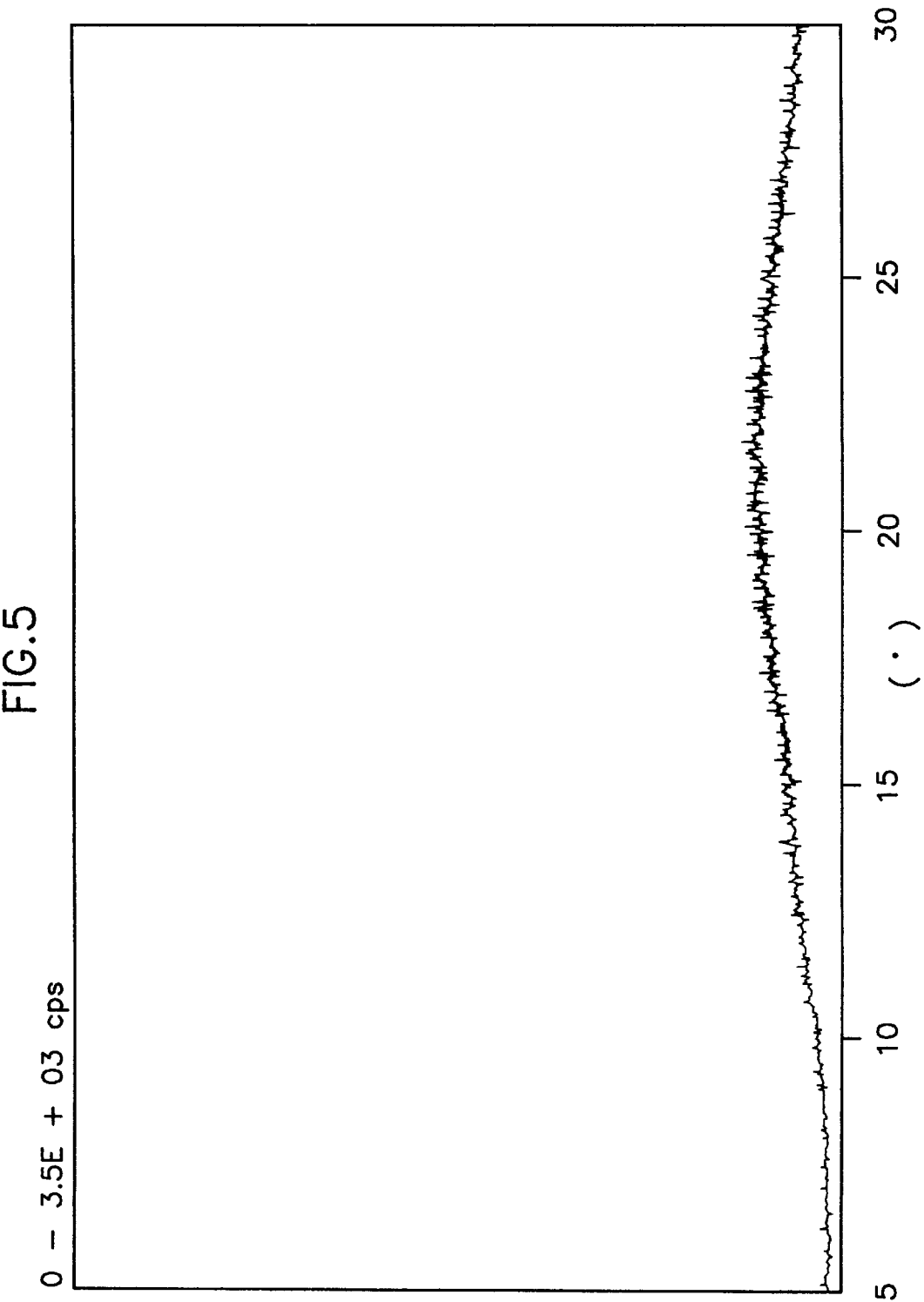
FIG. 5 is powder X-ray diffraction pattern of the Amorphous form.
Figure 6:
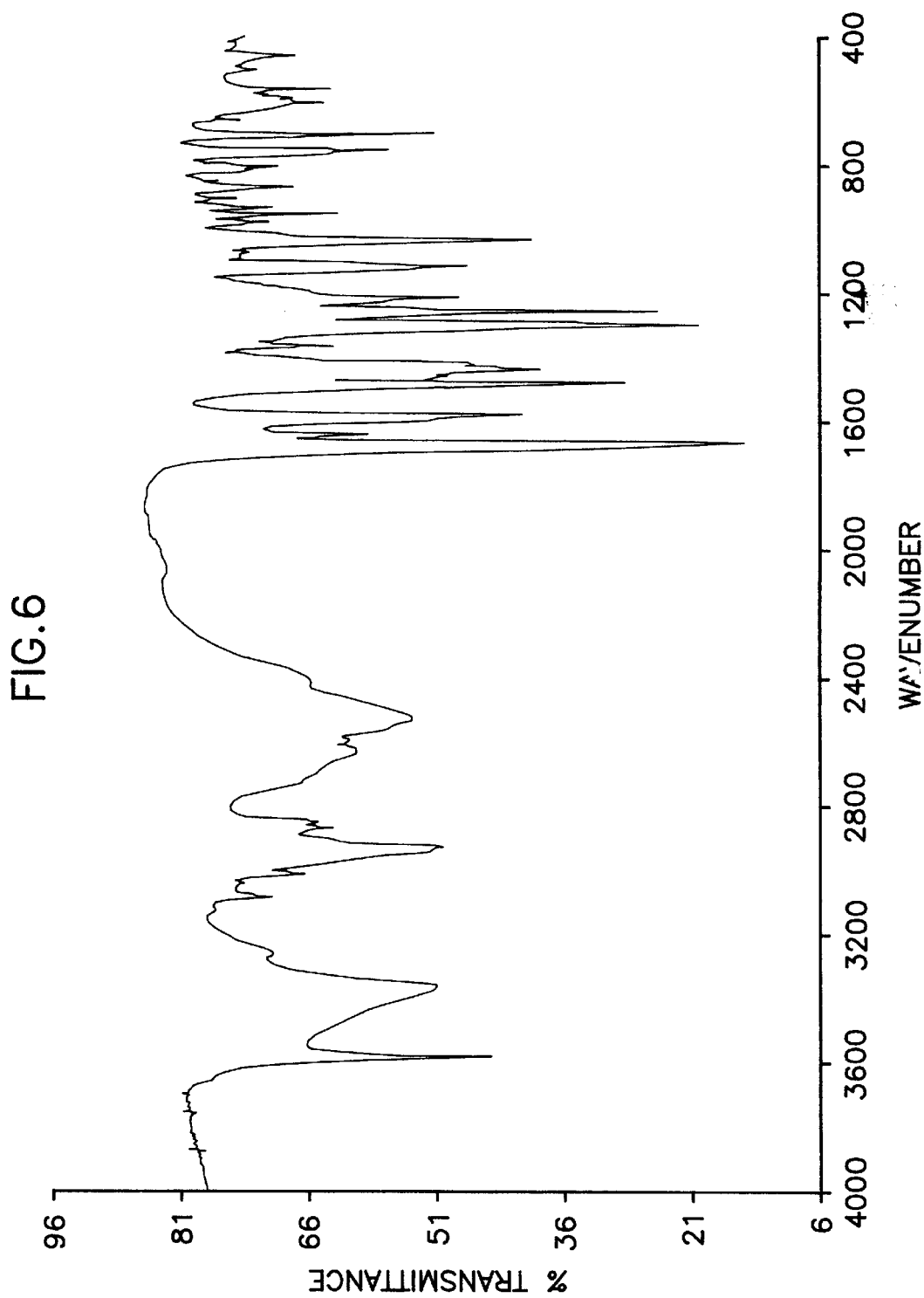
FIG. 6 is infrared absorption in potassium bromide of the polymorph (I).
Figure 7:
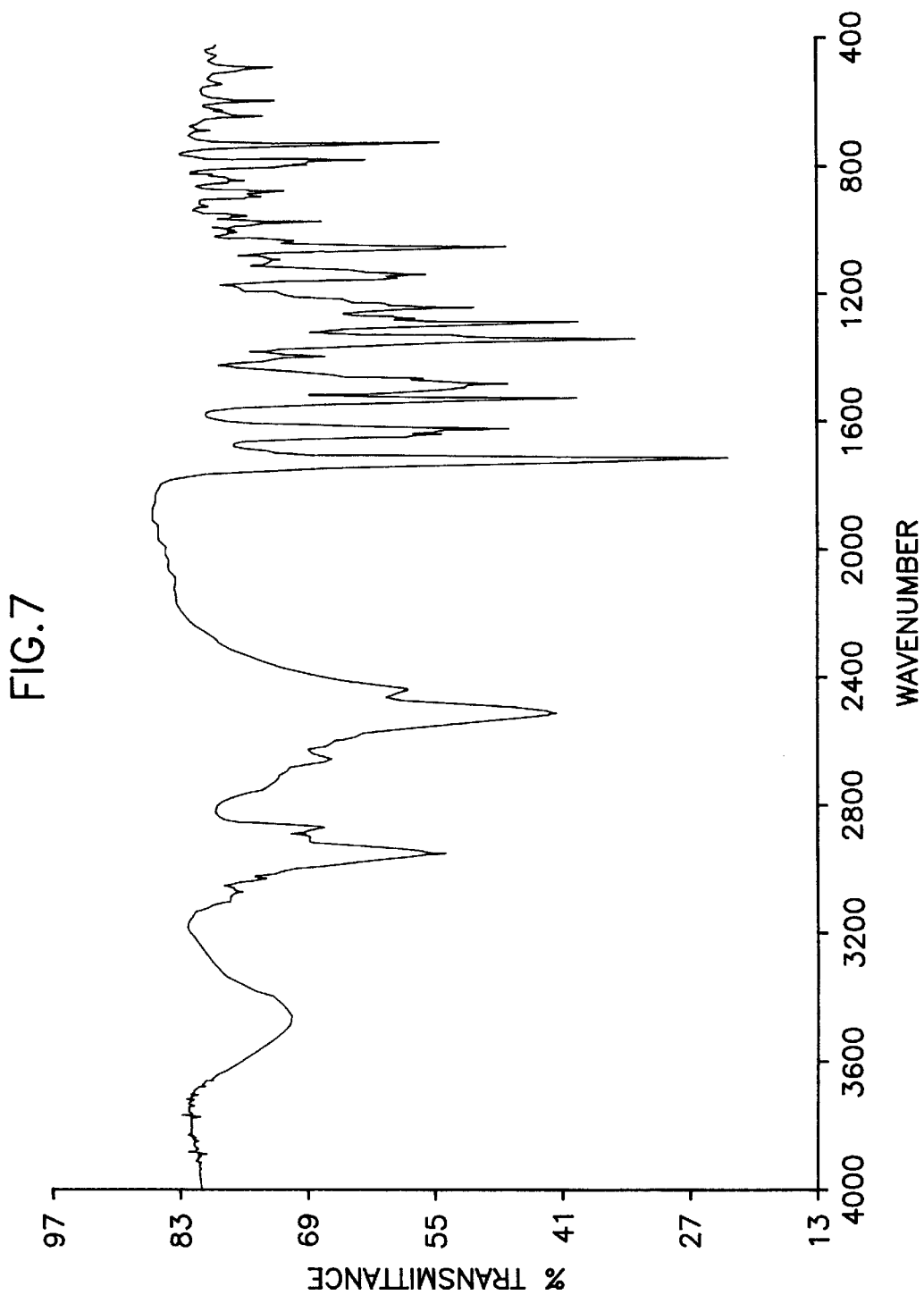
FIG. 7 is infrared absorption in potassium bromide of the polymorph (II).
Figure 8:
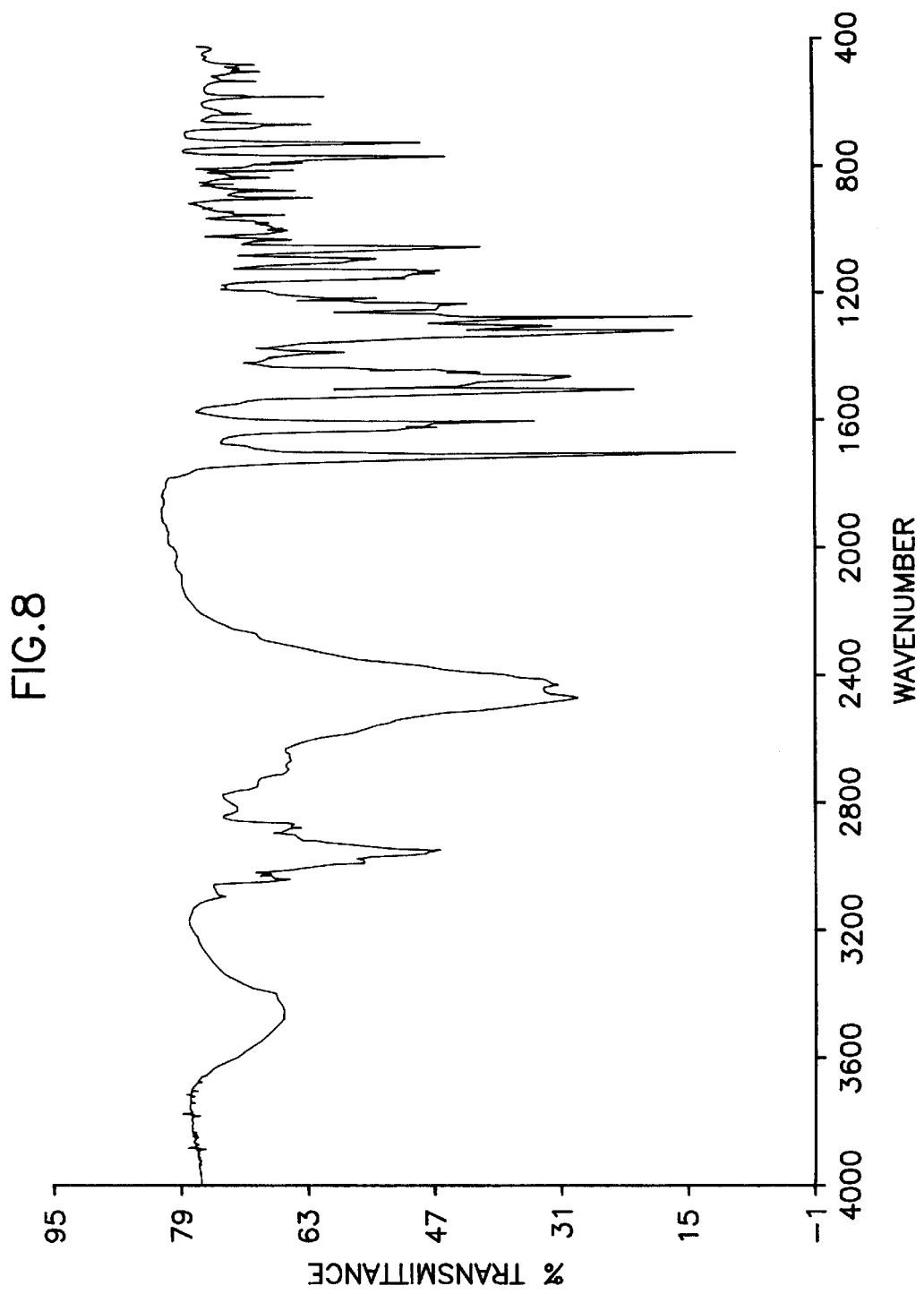
FIG. 8 is infrared absorption in potassium bromide of the polymorph (III).
Figure 9:
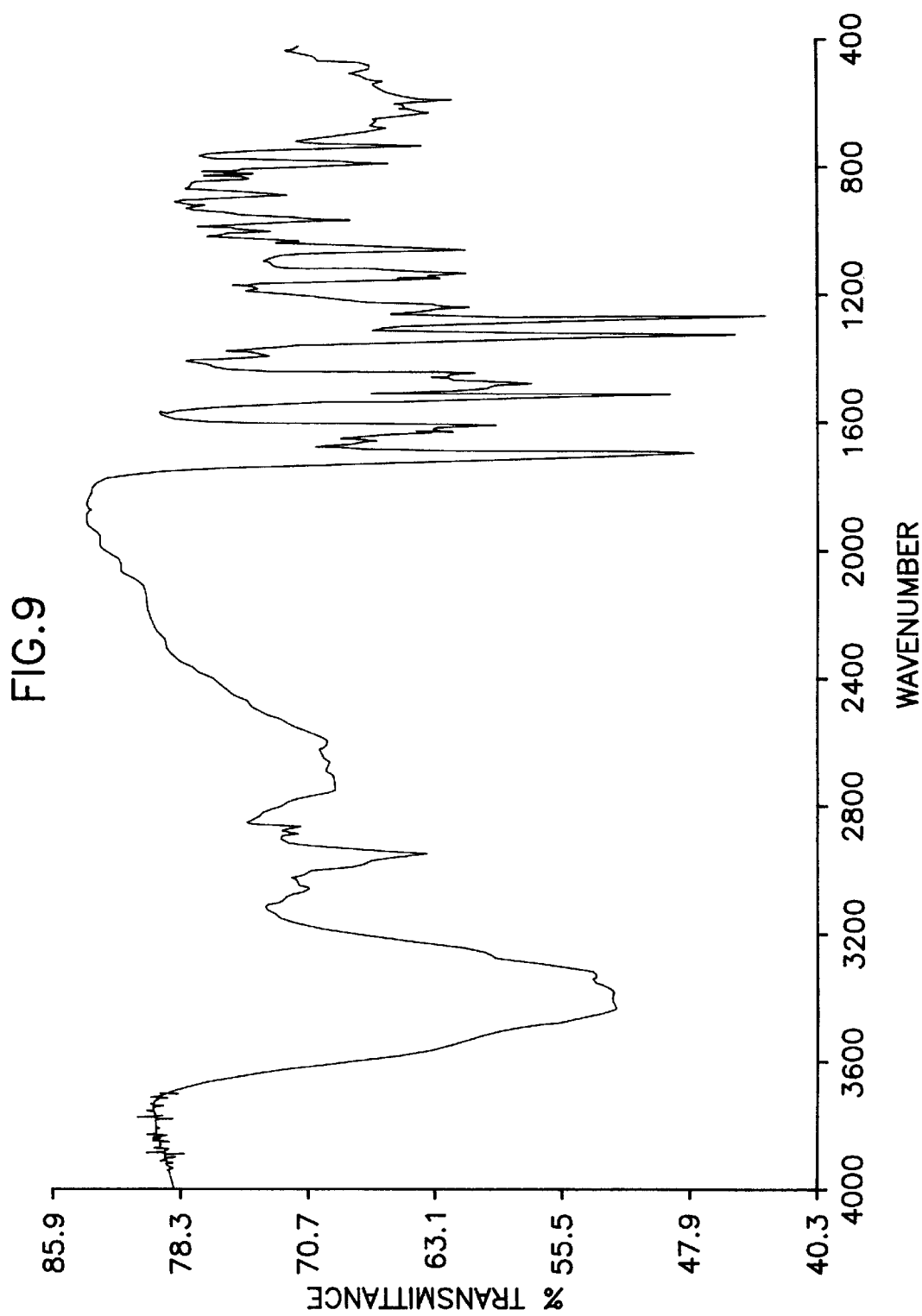
FIG. 9 is infrared absorption in potassium bromide of the polymorph (IV).
Figure 10:
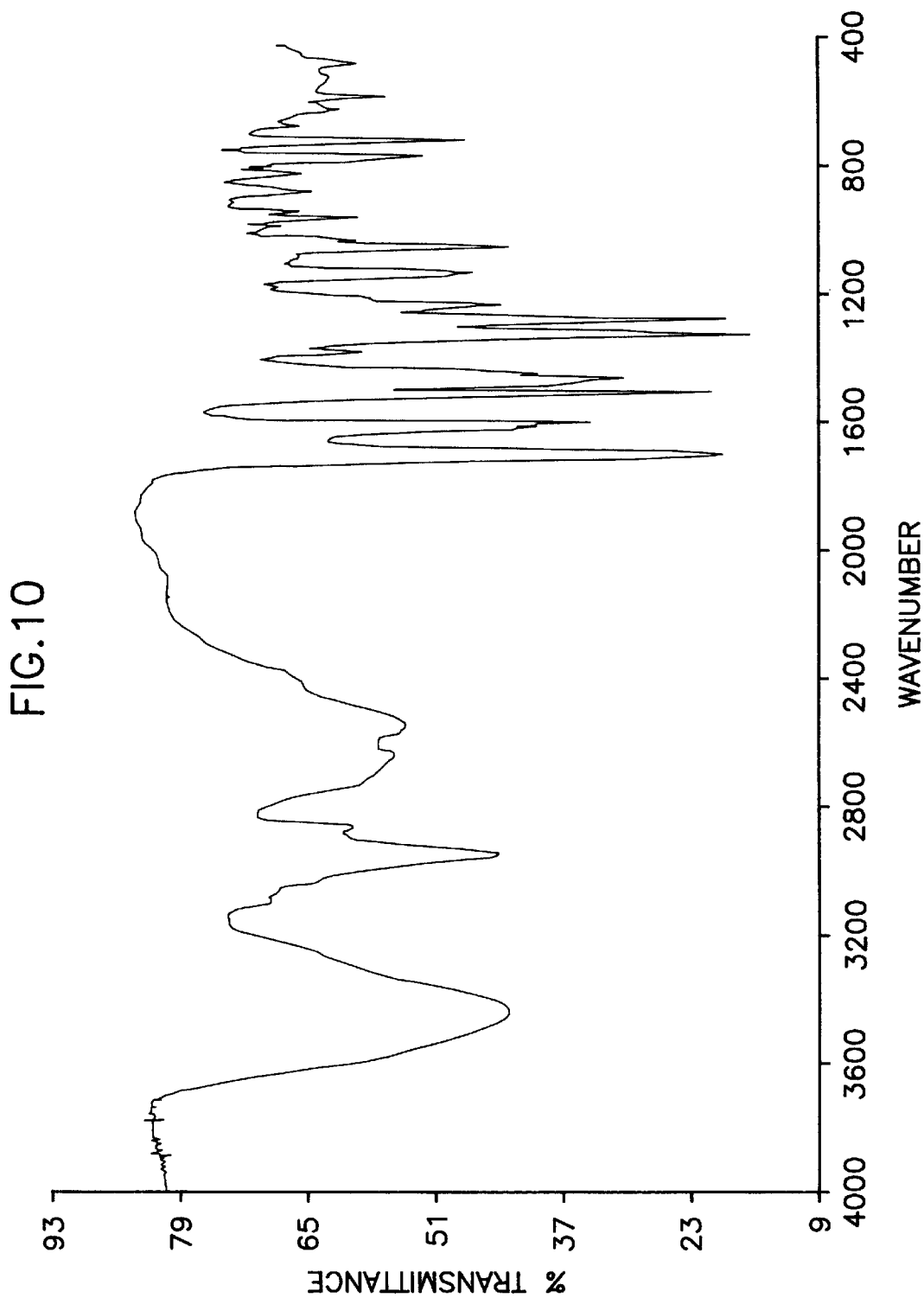
FIG. 10 is infrared absorption in potassium bromide of the amorphous form.
Figure 11:
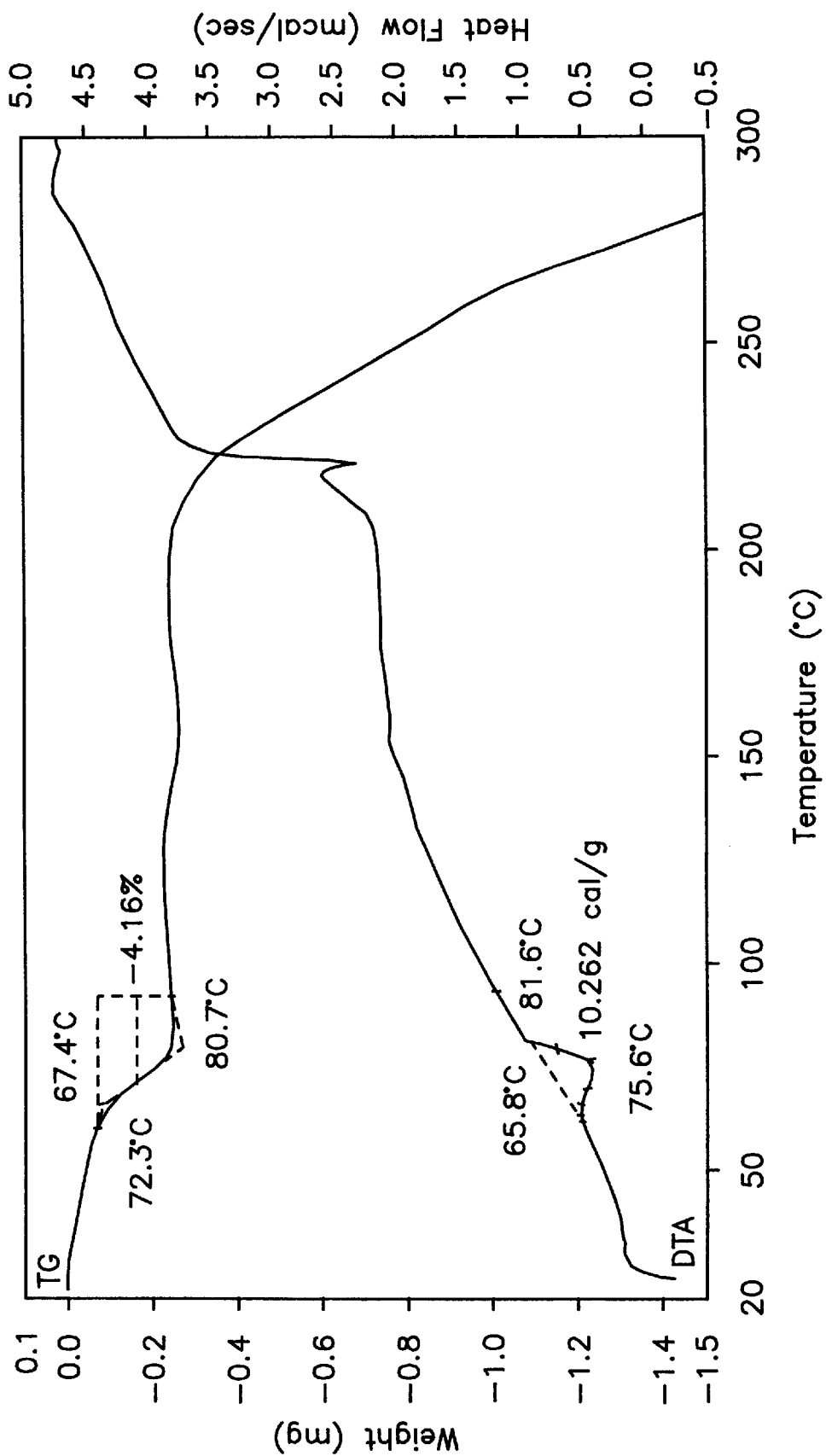
FIG. 11 is thermogravimetric and differential thermal analysis (TG-DTA) of the polymorph (I).
Figure 12:
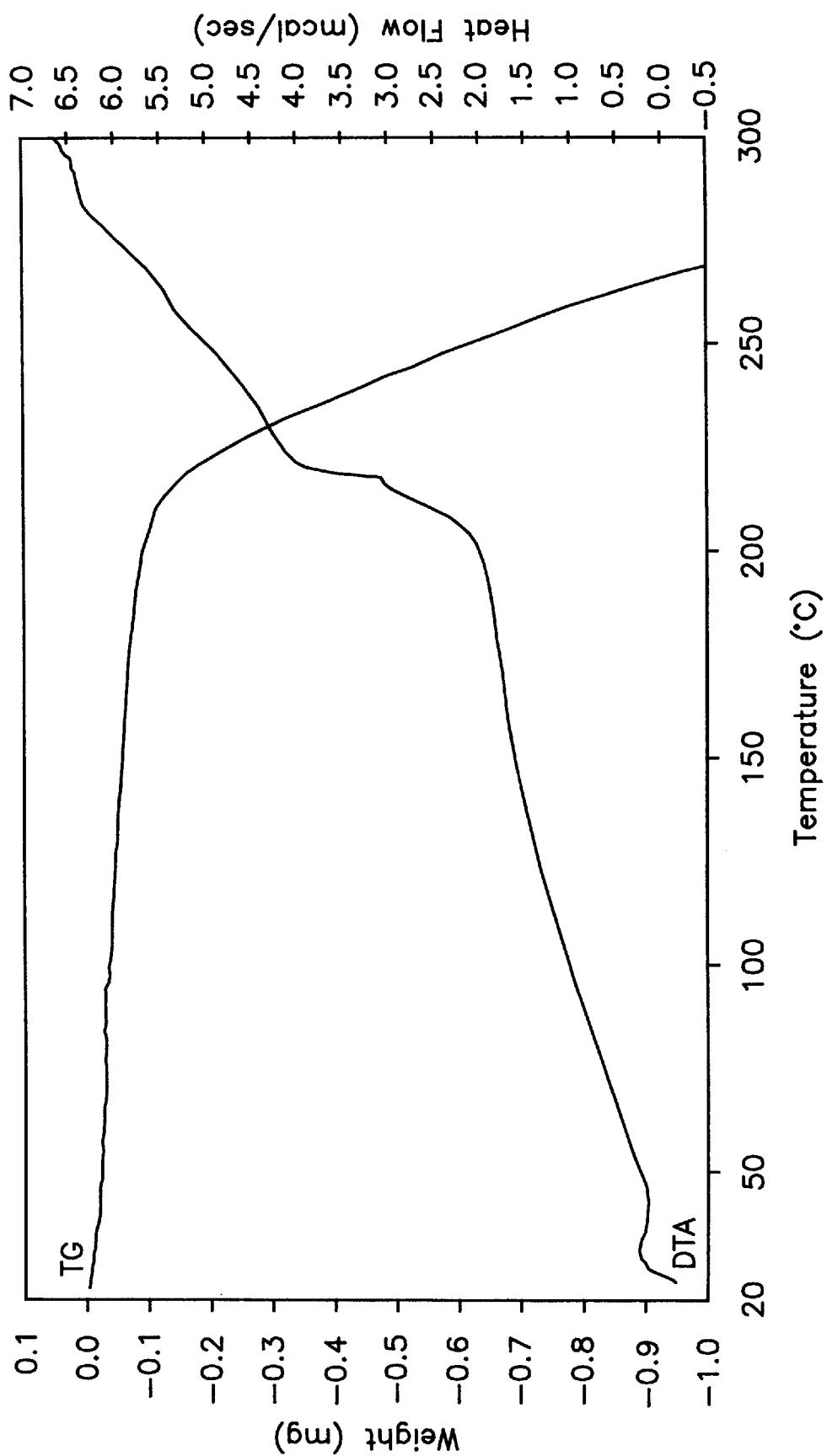
FIG. 12 is thermogravimetric and differential thermal analysis (TG-DTA) of the polymorph (II).
Figure 13:
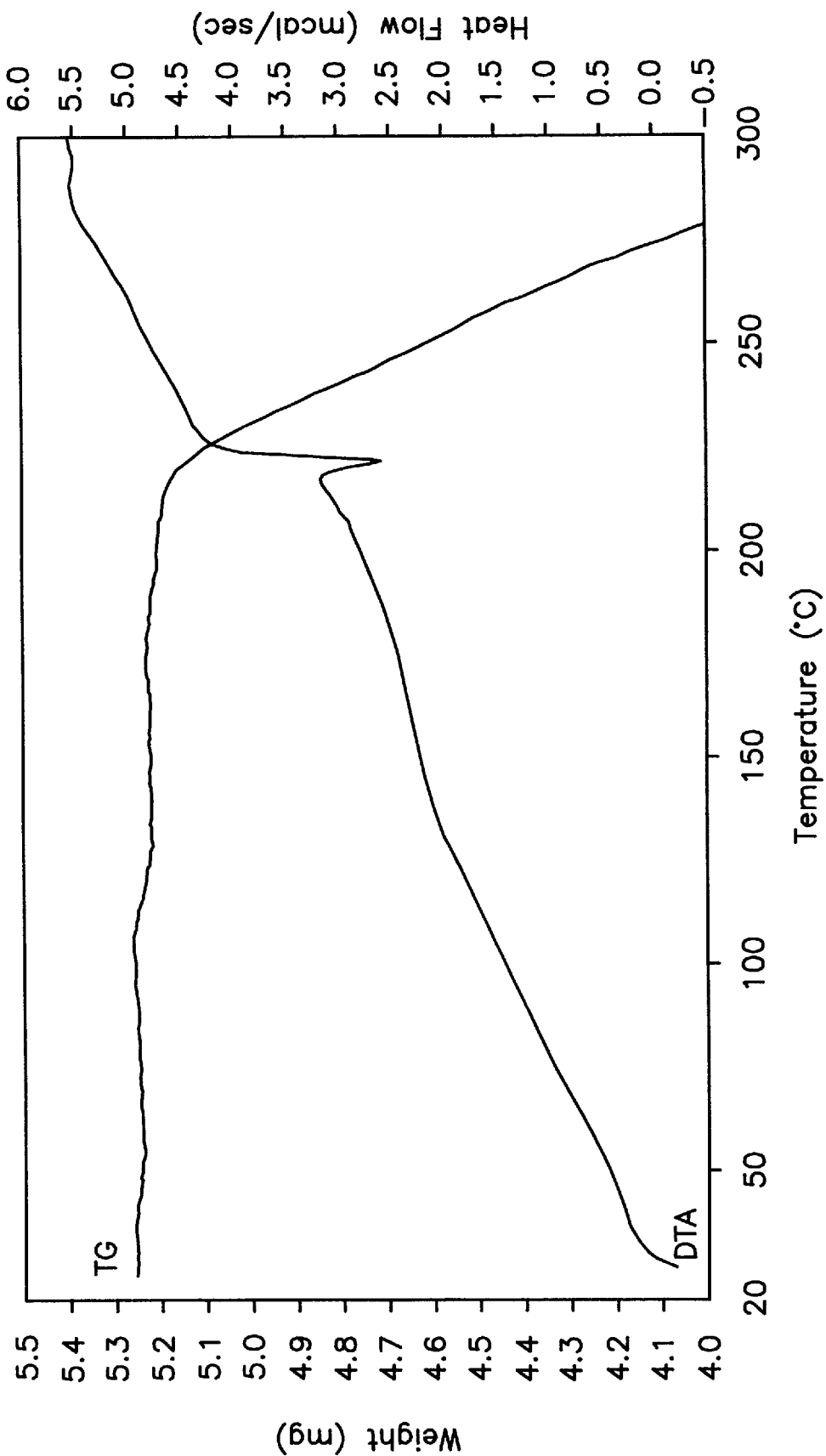
FIG. 13 is thermogravimetric and differential thermal analysis (TG-DTA) of the polymorph (III).
Figure 14:
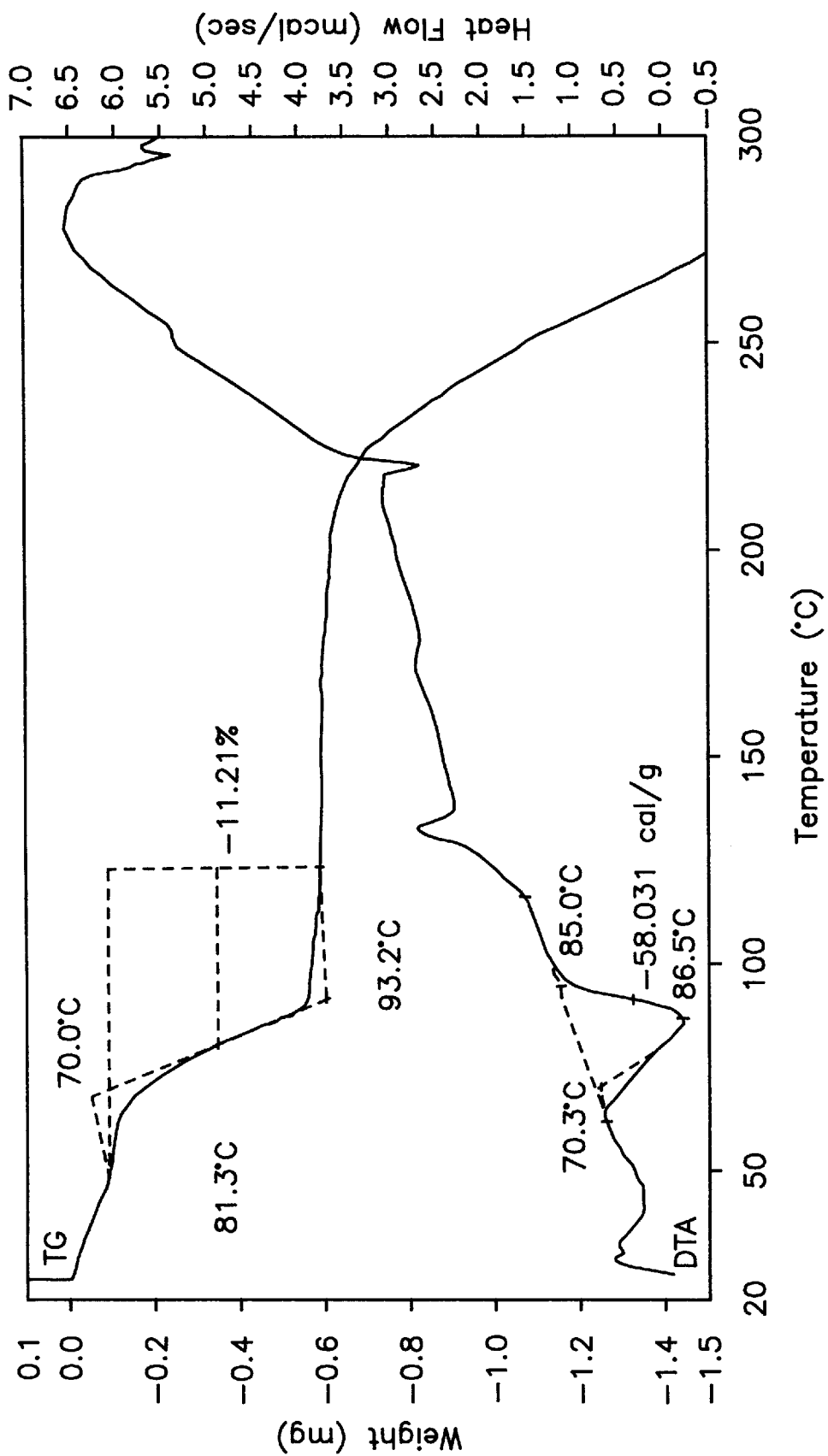
FIG. 14 is thermogravimetric and differential thermal analysis (TG-DTA) of the polymorph (IV).
Figure 15:
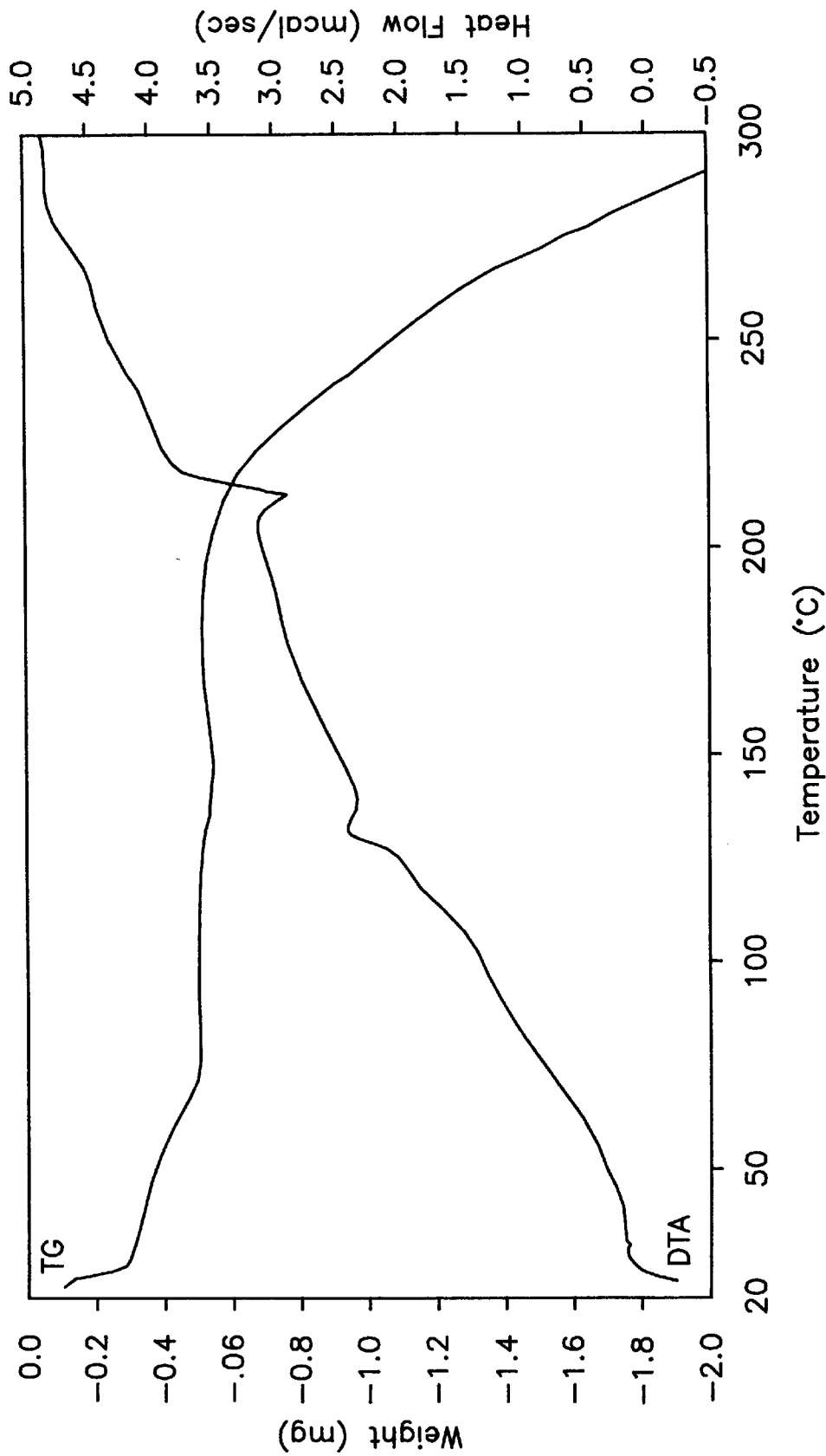
FIG. 15 is thermogravimetric and differential thermal analysis (TG-DTA) of the amorphous form.

The present invention will now be described in more detail with reference to the following Examples. It is needless to say that the technical scope of the present invention is not limited to these Examples.

Examples 1 to 8 relates to processes for preparing a polymorph (I).

Examples 9 to 15, processes for preparing a polymorph (II).

Examples 16 to 27, processes for preparing a polymorph (III).

Examples 28, process for preparing a polymorph (IV).

Reference Examples 1, process for preparing a amorphous form of Donepezil hydrochloride.

Example 1

Polymorph (I) of Donepezil Hydrochloride

One gram of Donepezil hydrochloride was dissolved in 5 ml of methanol. Adding 10 ml of diisopropyl ether and stirring the mixture in a bath containing ice water, filtration of the separated crystal and drying under atmosphere afforded 0.9 g of the title compound.

Example 2

Polymorph (I) of Donepezil Hydrochloride

One gram of Donepezil hydrochloride was dissolved in 5 ml of methanol under heating. After cooling to room temperature, 10 ml of isopropyl ether was added. Stirring was continued for 30 minutes at room temperature, then filtration of the separated crystal and drying under atmosphere afforded 0.9 g of the title compound.

Example 3

Polymorph (I) of Donepezil Hydrochloride

One gram of Donepezil hydrochloride was dissolved in 5 ml of methanol under heating. After initiation of cooling the solution, it started to separate crystal at 15° C. of the inner temperature. After 10 minutes, 10 ml of isopropyl ether was added. Stirring was continued for 1 hour at room temperature, then filtration of the separated crystal and drying under atmosphere afforded 0.9 g of the title compound.

Example 4

Polymorph (I) of Donepezil Hydrochloride 5 g of Donepezil hydrochloride was dissolved in 25 ml of methanol under heating, followed by cooling the mixture in a bath containing ice water. Filtration of the separated crystal and drying under atmosphere afforded 4.6 g of the title compound.

Example 5

Polymorph (I) of Donepezil Hydrochloride 0.3 g of Donepezil was dissolved in 1.5 ml of methanol, followed by addition of 0.97 ml of 10%-hydrochloric acid in methanol mixture. Filtration of the separated crystal and drying under atmosphere afforded 0.2 g of the title compound.

Example 6
Polymorph (I) of Donepezil Hydrochloride 0.3 g of Donepezil was dissolved in 3 ml of ethanol under heating, followed by addition of 3 ml of diisopropyl ether and 0.79 ml of 10%-hydrochloric acid in methanol mixture. Filtration of the separated crystal and drying under atmosphere afforded 0.2 g of the title compound.

Example 7
Polymorph (I) of Donepezil Hydrochloride 10 g of Donepezil was dissolved in 100 ml of ethanol under heating. Under stirring, a mixture of concentrated hydrochloric acid (3.1 g) and ethanol (28 ml) was added hereinto, followed by addition of 150 ml of diisopropyl ether. Filtration of the crystals after 10 seconds from the separation and drying under atmosphere afforded 9.36 g of the title compound with a yield of 85.4%, a water content of 5.17% and melting point of 225–226° C. (Decomposition).

Example 8
Polymorph (I) of Donepezil Hydrochloride 10 g of Donepezil hydrochloride was dissolved in 50 ml of methanol under heating. Under stirring in a bath containing ice water, 600 ml of diethyl ether was added. Stirring was continued for 1 hour in the same condition, then filtration of the crystals and drying under atmosphere afforded 10.0 g of the title compound.

Example 9
Polymorph (II) of Donepezil Hydrochloride 13.7 g of Donepezil and 4.4ml of hydrochloric acid were dissolved in 100 ml of ethanol under heating. Under stirring at room temperature, 200 ml of diisopropyl ether was added. Filtration of the crystals and drying under vacuum afforded 11.2 g of the title compound.

Example 10
Polymorph (II) of Donepezil Hydrochloride 50 g of Donepezil was dissolved in 200 ml of ethanol under heating. After cooling to room temperature, 27.3 g of 18%-hydrogen chloride in ethanol solution was added. After setting calmly for 1 hour, the mixture was concentrated under vacuum, then drying the obtained crystal under atmosphere afforded 55.0 g of the title compound.

Example 11
Polymorph (II) of Donepezil Hydrochloride 0.5 g of Donepezil was dissolved in 5 ml of ethanol under heating. Under stirring at room temperature, 1.31 ml of 10%-concentrated hydrochloric acid in ethanol was added, followed by addition of 5 ml of diisopropyl ether. Filtration of the crystals after 10 minutes from the separation and drying under atmosphere afforded 0.4 g of the title compound.

Example 12
Polymorph (II) of Donepezil Hydrochloride 5.6 g of Donepezil hydrochloride was dissolved in 30 ml of ethanol, followed by addition of 100 ml of diisopropyl ether. The mixture was cooled in a bath containing ice water. Then filtration of the crystals and drying at 50° C. for three days afforded 4.9 g of the title compound.

Example 13
Polymorph (II) of Donepezil Hydrochloride 23.3 g of Donepezil hydrochloride was dissolved in 250 ml of ethanol under heating. Under stirring in a bath containing ice water, 600 ml of diethyl ether was added. After setting calmly for 3 hours, filtration of the crystals and drying at 85° C. for 22 hours afforded 22.7 g of the title compound.

Example 14
Polymorph (II) of Donepezil Hydrochloride 10 g of Donepezil was dissolved in 100 ml of ethanol under heating. Under stirring, 150 ml of a mixture of concentrated hydrochloric acid (3.1 g) and ethanol (28 ml) was added, followed by addition of 150 ml of diisopropyl ether. Filtration of the crystals after 15 minutes from the separation and drying under atmosphere afforded 9.0 g of the title compound with a yield of 82.1% and melting point of 224–226° C. (Decomposition).

Example 15
Polymorph (II) of Donepezil Hydrochloride 40.0 g of Donepezil hydrochloride was dissolved in 700 ml of ethanol under heating. Under cooling in a bath containing ice water, 500 ml of diisopropyl ether was added, and crystallization was done by rubbing the flask wall with spatula. Then filtration of the crystals and drying at 50° C. for 12 hours afforded 31.4 g of the title compound.

Example 16
Polymorph (III) of Donepezil Hydrochloride 161 g of Donepezil hydrochloride was dissolved in 2000 ml of ethanol under heating. After cooling to room temperature, 5000 ml of diethyl ether was added under stirring. Then filtration of the crystals and drying at 35° C. for 12 hours afforded 120 g of the title compound with a yield of 74.5% and a water content of 0.15%.

Example 17
Polymorph (III) of Donepezil Hydrochloride 308 g of Donepezil was dissolved in 700 ml of ethanol. Under stirring, 230 ml of 10%-hydrogen chloride in ethanol solution and 5000 ml of diethyl ether were added successively. Filtration of the crystals and drying at 50° C. for 1 hour, then at 60° C. for 30 minutes, then at 85° C. for 12 hours afforded 269 g of the title compound.

Example 18
Polymorph (III) of Donepezil Hydrochloride 59 g of Donepezil was dissolved in 590 ml of ethanol. Under cooling in a bath containing ice water, 17.8 g of concentrated hydrochloric acid and 885 ml of diisopropyl ether were added successively. After stirring over night at room temperature, filtration of the crystals and drying at 55° C. for 22 hours afforded 62 g of the title compound.

Example 19
Polymorph (III) of Donepezil Hydrochloride 5 g of Donepezil hydrochloride was dissolved in 100 ml of ethanol under heating. After cooling to room temperature, 100 ml of n-hexane was added hereinto under stirring, followed by cooling in a bath containing ice water. Stirring was continued for 1 hour. Filtration of the crystals and drying at room temperature afforded 4 g of the title compound.

Example 20
Polymorph (III) of Donepezil Hydrochloride

One gram of Donepezil hydrochloride was dissolved in 15 ml of dichloromethane under heating. After cooling to room temperature, 15 ml of n-hexane was added hereinto under stirring, followed by cooling in a bath containing ice water. Stirring was continued for 1 hour. Filtration of the crystals and drying at room temperature afforded 0.9 g of the title compound.

Example 21
Polymorph (III) of Donepezil Hydrochloride 0.5 g of Donepezil was dissolved in 10 ml of acetone under heating. Under stirring at room temperature, 0.13 ml of concentrated hydrochloric acid was added hereinto. Stirring was continued for 30 minutes. Filtration of the crystals and drying at 85° C. for 16 hours afforded 0.5 g of the title compound.

Example 22
Polymorph (III) of Donepezil Hydrochloride 0.3 g of Donepezil was dissolved in 3 ml of ethyl acetate under heating. Under stirring at room temperature, 0.79 ml of 10%-hydrogen chloride in ethanol solution was added. Filtration of the crystals and drying at 85° C. for 3 hours, then at 70° C. for 16 hours afforded 0.3 g of the title compound.

Example 23
Polymorph (III) of Donepezil Hydrochloride 10 g of Donepezil was dissolved in 100 ml of ethanol under heating. Under stirring, a mixture of 3.1 g of concentrated hydrochloric acid and 28 ml of ethanol and then 150 ml of diisopropyl ether were added successively. Stirring was continued for 1 hour from the separation of crystals. Filtration of the crystals and drying at room temperature afforded 9.86 g of the title compound with a yield of 90%, a water content of 0.26% and melting point of 229–231° C. (Decomposition).

Example 24
Polymorph (III) of Donepezil Hydrochloride 5.0 g of The polymorph (I) of Donepezil hydrochloride was spread on a laboratory dish (Schale) and was allowed to stand or 7 days under ventilation of air at 85° C. 4.9 g of the title compound was obtained.

Example 25
Polymorph (III) of Donepezil Hydrochloride 5.0 g of the polymorph (I) of Donepezil hydrochloride was spread on a laboratory dish (Schale) and was allowed to stand for 2 days under ventilation of air at 85° C., then for 3 days under ventilation of air at 105° C. 4.8 g of the title compound was obtained.

Example 26
Polymorph (III) of Donepezil Hydrochloride 5.0 g of The polymorph (I) of Donepezil hydrochloride was spread on a laboratory dish (Schale) and was allowed to stand for 5 days under ventilation of air at 85° C. 4.9 g of the title compound was obtained.

Example 27
Polymorph (III) of Donepezil Hydrochloride 5.0 g of the polymorph (I) of Donepezil hydrochloride was spread on a laboratory dish (Schale) and was allowed to stand for 3 days under ventilation of air at 105° C. 4.9 g of the title compound was obtained.

Example 28
Polymorph (IV) of Donepezil Hydrochloride 15.0 g of the polymorph (II) of Donepezil hydrochloride was spread on a laboratory dish (Schale) and was continued to stand for 2 weeks under atmosphere having a relative humidity of 100%. 14.8 g of the title compound was obtained with melting point of 226–228° C. (Decomposition).

Reference Examples 1
Amorphous Form of Donepezil Hydrochloride 15.0 g of Donepezil hydrochloride was dissolved in 300 ml of water. The solution was frozen in a bath containing dry ice and acetone and freezing-dried (lyophilizated) for 4 days at −82° C. 14.8 g of the title compound was obtained.

Finally, the efficacy of the present invention in view of the stability or hygroscopicity will now be described in comparison with amorphous form of Donepezil hydrochloride. The invention provides advantageous results as follows:

(1) Stability Assay
Method for Measurement 10 mg of each of the polymorphs (I) to (IV) of Donepezil hydrochloride was taken as a couple of samples into tubes, respectively. They were stored under the following conditions and impurity's contents were measured periodically.

| Condition | Storage Period | | | |
|---|---|---|---|---|
| 80° C. | 1 week | 2 weeks | | |
| 60° C. | | 2 weeks | 1 month | |
| 40° C. | | | 1 month | 3 months |
| −20° C. | 1 week | 2 weeks | 1 month | 3 months |

Method and Condition for Measurement of HPLC Purity 10 ml of the following mobile phase for HPLC was added into each tube of the aforementioned samples. Then impurity's contents were measured for each sample under the following conditions. The average was calculated from two results.

| | |
|---|---|
| Column (Solid phase) | Inertsil ODS-II (4.6 mmI.D. × 150 mm) |
| Mobile Phase | $CH_3CN$/water/70% $HClO_4$ (V/V/V = 300:700:1) |
| Detector | UV271 nm |
| Flow rate | 1.0 ml/min. |
| Injection Volume | 5 ml |
| Column Temperature | room temperature |

Figure 16:
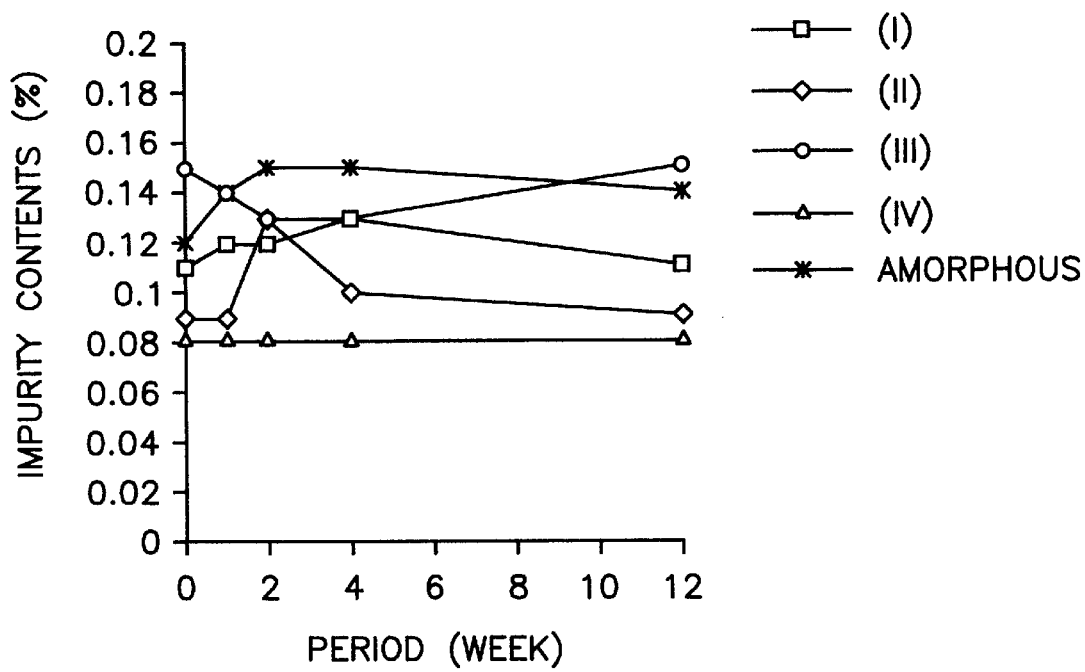
FIG. 16 is change of impurity contents for each polymorphs and amorphous form stored at −20° C.
Figure 17:
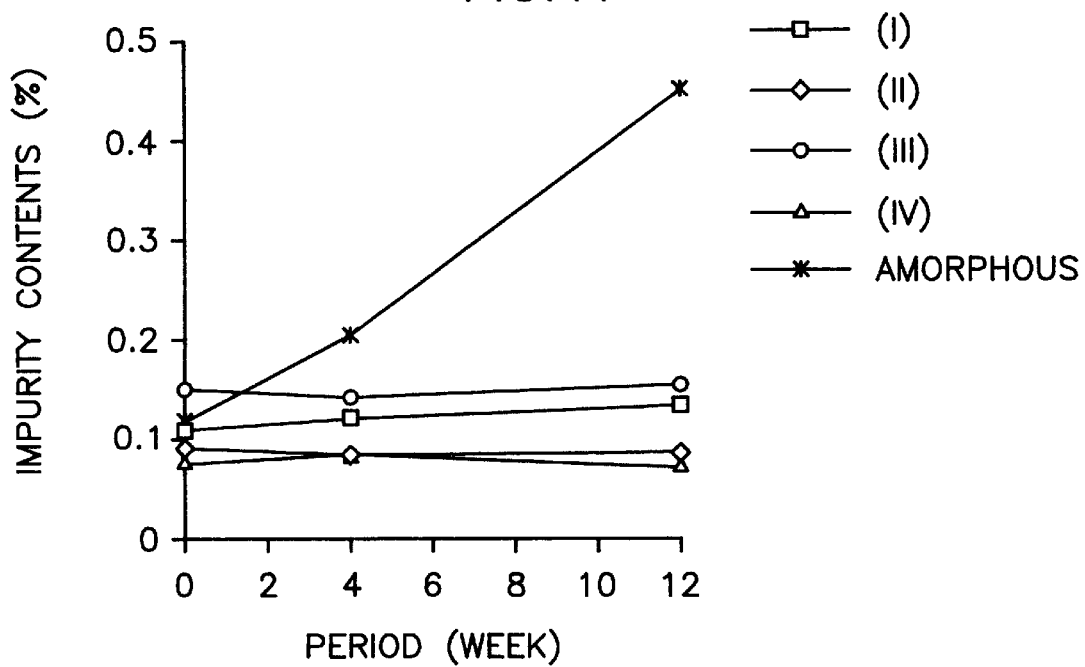
FIG. 17 is change of impurity contents for each polymorphs and amorphous form stored at 40° C.

Results:

| Impurity(%) | 0 | 1 week | 2 weeks | 1 month | 3 months |
|---|---|---|---|---|---|
| 1) Storage at −20° C. (refer to FIG. 16) | | | | | |
| Polymorph (I) | 0.11 | 0.12 | 0.12 | 0.13 | 0.11 |
| Polymorph (II) | 0.09 | 0.09 | 0.13 | 0.10 | 0.09 |
| Polymorph (III) | 0.15 | 0.14 | 0.13 | 0.13 | 0.15 |
| Polymorph (IV) | 0.08 | 0.08 | 0.08 | 0.08 | 0.08 |
| Amorphous | 0.12 | 0.14 | 0.15 | 0.15 | 0.14 |
| 2) Storage at 40° C. (refer to FIG. 17) | | | | | |
| Polymorph (I) | 0.11 | | | 0.12 | 0.13 |
| Polymorph (II) | 0.09 | | | 0.08 | 0.08 |
| Polymorph (III) | 0.15 | | | 0.14 | 0.15 |
| Polymorph (IV) | 0.08 | | | 0.08 | 0.07 |

-continued

Figure 18:
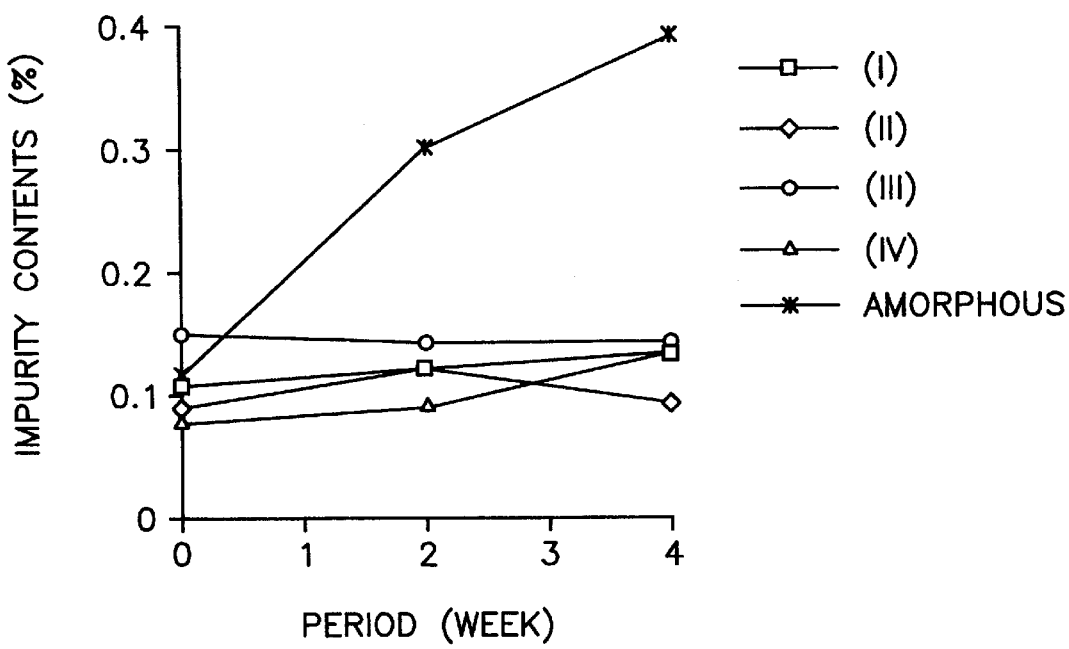
FIG. 18 is change of impurity contents for each polymorphs and amorphous form stored at 60° C.
Figure 19:
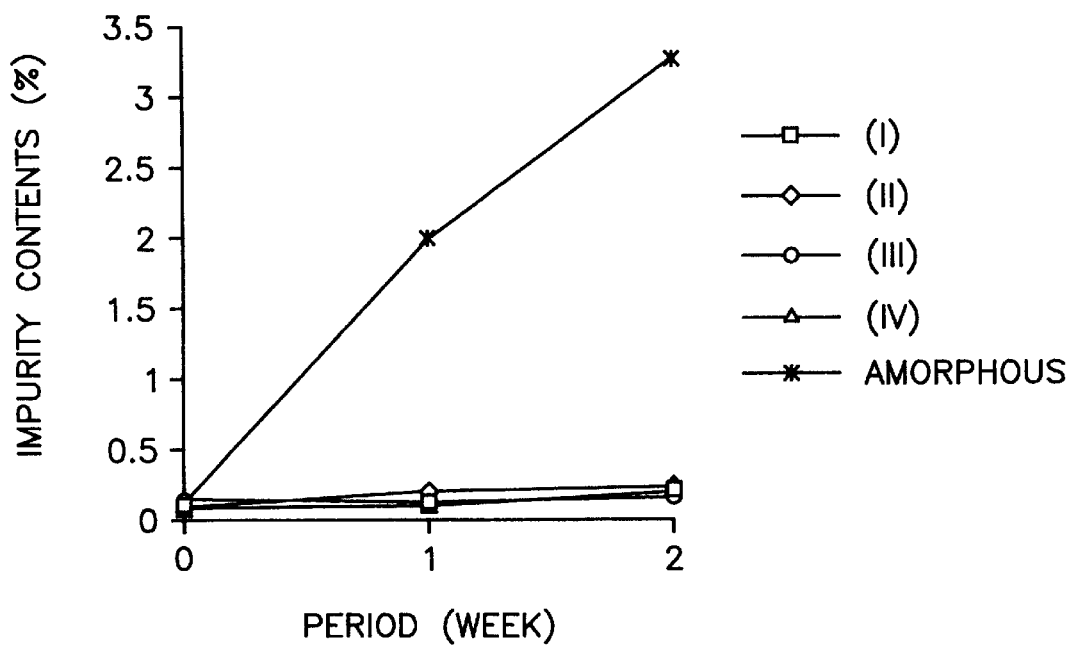
FIG. 19 is change of impurity contents for each polymorphs and amorphous form stored at 80° C.

| Impurity(%) | 0 | 1 week | 2 weeks | 1 month | 3 months |
|---|---|---|---|---|---|
| Amorphous | 0.12 | | | 0.20 | 0.45 |
| 3) Storage at 60° C. (refer to FIG. 18) | | | | | |
| Polymorph (I) | 0.11 | | 0.12 | 0.13 | |
| Polymorph (II) | 0.09 | | 0.12 | 0.09 | |
| Polymorph (III) | 0.15 | | 0.14 | 0.14 | |
| Polymorph (IV) | 0.08 | | 0.09 | 0.13 | |
| Amorphous | 0.12 | | 0.30 | 0.39 | |
| 4) Storage at 80° C. (refer to FIG. 19) | | | | | |
| Polymorph (I) | 0.11 | 0.12 | 0.19 | | |
| Polymorph (II) | 0.09 | 0.20 | 0.22 | | |
| Polymorph (III) | 0.15 | 0.14 | 0.14 | | |
| Polymorph (IV) | 0.08 | 0.09 | 0.19 | | |
| Amorphous | 0.12 | 2.02 | 3.29 | | |

It is evident from the above results that the polymorphs (I) to (IV) is superior in stability against heat to the amorphous form.

(2) Hygroscopicity Assay

Method for Measurement

Polymorphs (I) to (IV) were stored under atmosphere having the following relative humidities at 25° C. Water contents were measured according to the general method (Karl Fischer Method) introduced by the Japanese Pharmacopoeia.

Figure 20:
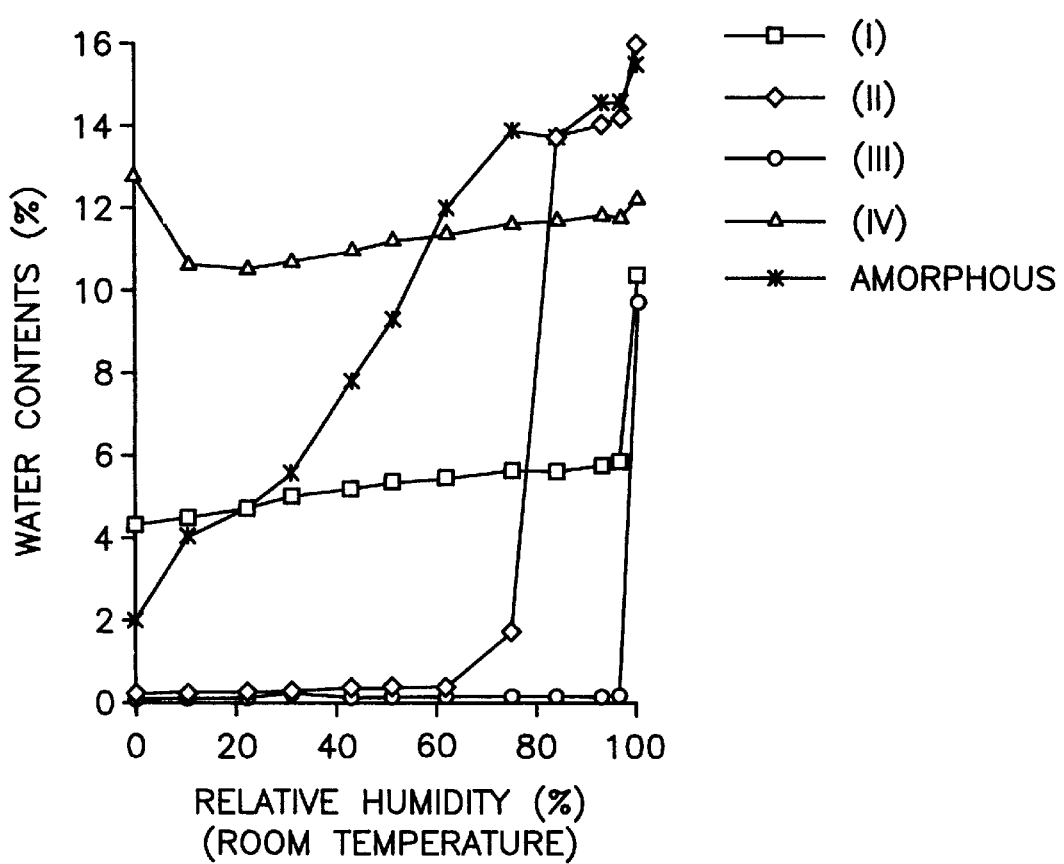
FIG. 20 is water contents for each polymorphs and amorphous form stored at 25° C. under various relative humidity condition.

Results (refer to FIG. 20)

| Relative Humidity | Water Contents (%) Polymorph | | | | |
|---|---|---|---|---|---|
| (%) | (I) | (II) | (III) | (IV) | Amorphous |
| Initiation | 4.34 | 0.26 | 0.11 | 12.87 | 2.03 |
| 10.6 | 4.54 | 0.28 | 0.15 | 10.70 | 4.09 |
| 22.2 | 4.75 | 0.29 | 0.14 | 10.60 | 4.78 |
| 31.0 | 5.07 | 0.32 | 0.26 | 10.77 | 5.61 |
| 42.8 | 5.25 | 0.39 | 0.13 | 11.03 | 7.80 |
| 51.0 | 5.38 | 0.43 | 0.15 | 11.28 | 9.29 |
| 61.8 | 5.49 | 0.40 | 0.18 | 11.40 | 12.01 |
| 75.0 | 5.65 | 1.73 | 0.15 | 11.62 | 13.89 |
| 84.0 | 5.64 | 13.70 | 0.16 | 11.72 | 13.74 |
| 93.0 | 5.76 | 13.99 | 0.15 | 11.84 | 14.51 |
| 96.6 | 5.88 | 14.18 | 0.17 | 11.80 | 14.53 |
| 100.0 | 10.37 | 15.93 | 9.71 | 12.26 | 15.44 |

In the above results, the polymorphs (I) to (IV) did not show hygroscopicity until a relative humidity of 96.6%, until 75.0%, until 96.6%, until 100%, respectively. The amorphous Donepezil hydrochloride showed hygroscopicity at and thereafter 10.6%. Those experimental results show that the polymorphs of Donepezil hydrochloride (I) to (IV) have an excellent heat stability and a low hygroscopicity.

What is claimed is:

1. Donepezil hydrochloride, 1-benzyl-4-[(5,6-dimethoxy-1-indanon)-2-yl]methylpiperidine hydrochloride, in the form of a polymorph being specified by peaks at below shown diffraction degrees with the below shown intensity in terms of $I/I_o$ in X-ray powder diffraction pattern and the below shown absorption peaks in infrared absorption spectra in potassium bromide in terms of reciprocal centimeters:

Polymorph (III) Exhibiting peaks in the powder X-ray diffraction pattern as follows:

| Diffraction angles (2θ, °) | Intensity (I/I$_o$) |
|---|---|
| 6.56 | 30 |
| 9.94 | 8 |
| 13.00 | 17 |
| 15.00 | 47 |
| 15.26 | 14 |
| 15.74 | 6 |
| 16.48 | 35 |
| 17.42 | 4 |
| 18.10 | 21 |
| 18.50 | 56 |
| 19.50 | 17 |
| 20.10 | 32 |
| 20.94 | 21 |
| 21.66 | 100 |
| 22.32 | 25 |
| 22.92 | 17 |
| 23.92 | 19 |
| 24.68 | 17 |
| 26.00 | 44 |
| 27.20 | 23 |
| 28.02 | 29 |
| 28.22 | 40 |
| 28.60 | 13 |

Wave numbers ($cm^{-1}$) of infrared absorption spectra in potassium bromide are:
559, 641, 648, 702, 749, 765, 786, 807, 851, 872, 927, 949, 966, 975, 982, 1007, 1034, 1071, 1080, 1111, 1119, 1131, 1177, 1190, 1205, 1217, 1230, 1250, 1265, 1292, 1313, 1367, 1389, 1420, 1438, 1453, 1461, 1470, 1500, 1589, 1605, 1697, 2407, 2419, 2461, 2624, 2641, 2651, 2667, 2837, 2848, 2924, 2954, 2961, 2993, 3007, 3377, 3433 $cm^{-1}$.

2. A process for producing the polymorph (III) of Donepezil hydrochloride as defined in claim 1, which comprises the steps of dissolving Donepezil hydrochloride in ethanol and adding diethyl ether to the solution.

3. A process for producing the polymorph (III) of Donepezil hydrochloride as defined in claim 1, which comprises the steps of dissolving Donepezil hydrochloride in methylene chloride and adding n-hexane to the solution.

4. A process for producing the polymorph (III) of Donepezil hydrochloride as defined in claim 1, which comprises the steps of dissolving Donepezil in acetone and adding hydrochloric acid or hydrogen chloride to the solution.

5. A process for producing the polymorph (III) of Donepezil hydrochloride as defined in claim 1, which comprises the steps of dissolving Donepezil in ethyl acetate and adding hydrochloric acid or hydrogen chloride to the solution.

6. A process for producing the polymorph (III) of Donepezil hydrochloride as defined in claim 1, which comprises the steps of dissolving Donepezil in ethanol, adding hydrochloric acid or hydrogen chloride to the solution and adding to the mixture a solvent selected from diethyl ether, isopropyl ether and n-hexane.

7. The process as claimed in claim 6, in which the solvent is isopropyl ether and the crystalline precipitates are filtrated in one or more hours after they have precipitated.

8. A method for treating a disease accompanied by acetylcholinesterase activity which comprises administering to a human patient in need thereof a pharmacologically effective amount of the donepezil hydrochloride in the form of the polymorph as defined in claim 1 for inhibiting the acetylcholinesterase activity.

9. The method as claimed in claim 8, in which the disease is senile dementia.

10. The method as claimed in claim 8, in which the disease is senile dementia of the Alzheimer type.

11. A therapeutical composition which comprises a pharmacologically effective amount of Donepezil hydrochloride in the form of the polymorph as defined in claim 1 and a pharmacologically acceptable carrier.

12. A process for producing the polymorph (III) of Donepezil hydrochloride as defined in claim 1, which comprises the step of heating the polymorph (I) or (II), each polymorph being specified by peaks at the below shown diffraction degrees with the below shown intensity in terms of $I/I_o$ in X-ray powder diffraction pattern and the below shown absorption peaks in infrared absorption spectra in potassium bromide in terms of reciprocal centimeters:

(1) Polymorph (I) exhibiting peaks in the powder X-ray diffraction pattern area as follows:

| Diffraction angles ($2\theta$, °) | Intensity ($I/I_o$) |
|---|---|
| 9.94 | 24 |
| 10.60 | 19 |
| 12.66 | 69 |
| 13.12 | 55 |
| 13.66 | 44 |
| 13.86 | 40 |
| 14.92 | 49 |
| 15.26 | 17 |
| 16.08 | 35 |
| 16.86 | 34 |
| 17.50 | 34 |
| 17.58 | 42 |
| 18.42 | 20 |
| 19.28 | 27 |
| 19.80 | 45 |
| 19.94 | 45 |
| 21.22 | 100 |
| 22.00 | 32 |
| 22.54 | 31 |
| 22.98 | 49 |
| 23.60 | 56 |
| 23.78 | 75 |
| 23.92 | 78 |
| 26.46 | 33 |
| 28.02 | 25 |
| 29.50 | 37 |

Wave numbers (cm$^{-1}$) of infrared absorption spectra in potassium bromide are:
463, 502, 563, 589, 604, 701, 750, 759, 799, 860, 922, 947, 972, 1012, 1038, 1104, 1120, 1128, 1175, 1192, 1218, 1250, 1267, 1316, 1368, 1410, 1433, 1440, 1455, 1472, 1502, 1591, 1606, 1644, 1684, 2412, 2530, 2559, 2595, 2620, 2717, 2840, 2858, 2924, 3004, 3074, 3259, 3373, 3547, 3589 cm$^{-1}$; or Polymorph (II) Exhibiting Peaks in the Powder X-ray Diffraction Pattern as Follows:

| Diffraction angles ($2\theta$, °) | Intensity ($I/I_o$) |
|---|---|
| 7.40 | 8 |
| 9.88 | 100 |
| 12.36 | 13 |
| 15.54 | 40 |
| 16.10 | 38 |
| 16.22 | 38 |
| 16.48 | 35 |
| 17.30 | 17 |
| 18.04 | 20 |
| 18.44 | 17 |
| 18.84 | 19 |
| 19.34 | 19 |
| 19.84 | 47 |
| 21.16 | 24 |
| 22.40 | 19 |
| 23.18 | 33 |
| 24.02 | 22 |
| 24.92 | 25 |
| 25.72 | 27 |
| 26.40 | 18 |
| 27.22 | 14 |

Wave numbers (cm$^{-1}$) of infrared absorption spectra in potassium bromide are:

699, 748, 762, 845, 947, 1009, 1035, 1067, 1103, 1118, 1129, 1174, 1193, 1206, 1222, 1247, 1267, 1317, 1365, 1422, 1436, 1456, 1465, 1502, 1592, 1607, 1688, 2412, 2489, 2627, 2846, 2868, 2913, 2928, 3435 cm$^{-1}$.

* * * * *

Disclaimer

6,140,321—Akio Imai; Hideaki Watanabe; Takashi Kajima; Yasushi Ishihama; Akiyo Ohtsuka; Tomohide Tanaka, all of Iraraki, Japan. POLYMORPHS OF DONEPEZIL HYDROCHLORIDE AND PROCESS FOR PRODUCTION. Patent dated October 31, 2000. Disclaimer filed May 22, 2006 by the Assignee, Elsai Co. Ltd.

Hereby enters this disclaimer to claims 1-12, 9 of said patent.

*(Official Gazette, June 19, 2007)*